(12) United States Patent
Kolmar et al.

(10) Patent No.: US 7,186,524 B2
(45) Date of Patent: Mar. 6, 2007

(54) METHOD FOR EXPOSING PEPTIDES AND POLYPEPTIDES ON THE CELL SURFACE OF BACTERIA

(75) Inventors: Harald Kolmar, Gottingen (DE); Andreas Christmann, Gottingen (DE); Alexander Wentzel, Gottingen (DE)

(73) Assignee: NascaCell Technologies AG, Munich (DE)

( * ) Notice: Subject to any disclaimer, the term of this patent is extended or adjusted under 35 U.S.C. 154(b) by 526 days.

(21) Appl. No.: 10/415,165

(22) PCT Filed: Oct. 25, 2001

(86) PCT No.: PCT/DE01/04009

§ 371 (c)(1),
(2), (4) Date: Oct. 15, 2003

(87) PCT Pub. No.: WO02/34906

PCT Pub. Date: May 2, 2002

(65) Prior Publication Data

US 2004/0106118 A1    Jun. 3, 2004

(30) Foreign Application Priority Data

Oct. 26, 2000  (DE) ............... 100 53 224

(51) Int. Cl.
*C12P 21/06* (2006.01)
*C12N 1/20* (2006.01)
*C12N 15/00* (2006.01)

(52) U.S. Cl. ................ 435/69.1; 435/252.3; 435/320.1

(58) Field of Classification Search ............... 435/69.1, 435/252.3, 320.1
See application file for complete search history.

(56) References Cited

FOREIGN PATENT DOCUMENTS

| EP | 0 872 555 A1 | 2/1997 |
|---|---|---|
| WO | WO 97/40177 | 10/1997 |

OTHER PUBLICATIONS

Candy et al.; Characterization of the C-terminal domains of intimin-like proteins of enteropathogenic and enterohemorrhagic *Escherichia coli, Citrobacter freundii*, and *Hafnia alvei*; dated May 1994 Infection + Immunity 62 (5) pp. 1835-1842.

Christmann et al. The cystine knot of a squash -type protease inhibitor as a structural scaffold for *Escherichia coli* cell surface display of conformationally constrained peptides.Protein Engineering vol. 12. No. 9 pp. 797-806; dated 1999.

Schembri et al. XP-002109166'; Applied and Enviromental Microbiology, May 1998 pp. 1628-1633; vol. 64 No. 5 , Heterobinary Adhesins Based on the *Escherichia coli* Fim H Fimbrial Protein.

DNA Circular; XP-002211330; Expression vector for surface display of Intimin' fusion proteins on cells of *Escherichia coli*; dated Sep. 11, 2001.

Christmann et al. Journal of Immunological Methods 257 (2001) 163-173 Epitope mapping and affinity purification of monospecific antibodies by *Escherichia coli* cell surface display of gene derived random peptide libraries. dated Jul. 8, 2001.

Journal of Bacteriology, Dec. 2001 pp. 7273-7284 Wenzel et al., XP-002211329; Display of passenger proteins on the surface of *Escherichia coli* K-12 by the Enterohemorrhagic *E. coli* Intimin EaeA.

Nature Structural Biology, vol. 6, No. 6; Kelly et al. XP-001018419Structure of the cell- adhesion fragment of intimin from enteropathogenic *Escherichia coli*; dated Apr. 1999 pp. 313-318.

*Primary Examiner*—Mark Navarro
(74) *Attorney, Agent, or Firm*—Whitham Curtis Christofferson & Cook, PC

(57) ABSTRACT

The inventive method allows peptides or polypeptides to be exposed on the surface of gram-negative host bacteria using specific intimin-based anchor modules. Intimins with shortened carboxy terminals have been found to be particularly suitable anchor modules for passenger domains in the exterior *E. coli* cell membrane. According to the method, host bacteria are transformed using vectors, on which are located a fused nucleic acid sequence consisting of a sequence segment which codes for an intimin with a shortened carboxy terminal and a nucleic acid sequence segment which codes for the passenger peptide that is to be exposed. The invention permits a particularly large number of passenger domains to be exposed on the cell surface of the bacteria, without adversely affecting the viability of the bacteria.

19 Claims, 16 Drawing Sheets

```
                                                                                  XbaI
     tatttaccactccctatcagtgatagagaaagtgaaatgaatagttcgacaaaaatct
  61 ----------+---------+---------+---------+---------+---------+ 120
     ataaaatggtgagggatagtcactatctctttcacttatcaagctgttttaga Start Translation Intimin
     agataacgagggcaaaaaatgattactcatgttgttatacccggacccggcacaagcat
 121 ----------+---------+---------+---------+---------+---------+ 180
     tctattgctcccgttttttactaatgagtaccaacaatatgggcctgggccgtgttcgta
                       M  I  T  H  G  C  Y  T  R  T  R  H  K  H HpaI
     aagctaaaaacattgattatgctgttagtgctgaccaaatcctaacaaaaatacaatta
 181 ----------+---------+---------+---------+---------+---------+ 240
     ttcgatttttttgtaactaatacgactgattcacgactggtttaggattgttttatgttaat
      K  L  K  T  L  I  M  L  S  A  G  L  G  L  F  F  Y  V  N
     EcoRI                              DraI
                                          tttgatcaaaccaaggccagcgcaa
                                        ----------+---------+      2119
                                          aactagttttggttccggtcgcgtt
                                          F  D  Q  T  K  A  S  A  I
     tagaattcatttgcaaat                                                                //
 241 ----------+--------                                                               //
     atcttaagtaaacgttta
      *  N  S  F  A  N  G
                                                                                                              E-tag
      ttcctccaacgcccctggggtgcgccggtgcgccggtaccgtatccagatccgctgaaccgcgtgccg
 2120 ----------+---------+---------+---------+---------+---------+---------+ 2179
      aaggaggttgcggggaccccacgcggccacgcggccatggcatagggctctaggacttggcgcacggc
       P  P  T  P  P  L  G  A  P  V  P  Y  P  D  P  L  E  P  R  A  A
      SmaI
      cttctggccccgggtgcgatgaagcttaggtgaatatcgaaccatacgattcatcatgca
 2180 ----------+---------+---------+---------+---------+---------+ 2239
      gaagaccggggcccacgctacttcgaatcctactagcttgtatgctaagtagtacgt
       S  G  P  G  C  D  G  S  L  G  D  L  E  P  Y  D  S  C  K
```

Figure 2A

```
            SupE2_Ecoup
    GCGCGAATTCACC AGAAAGCGTT GTACGG
351            cacc agaaagcgtt gtacggatgg ggtatcgcca agcggtaagg
                                                             KpnI
401 caccggtttt tgataccggc attccctggt tcgaatccag gtacccagc
      tRNAGln (CCA)
451 catcttcttc gagtaagcgg ttcaccgccc ggttattggg gtatcgccaa
501 gcggtaaggc accggttttt gataccggca ttccctgtt cgaatccagg
      tRNAGln (CCT)
551 tacccagcc atcgaagaaa caatctggct acgtagctca gttggttaga
601 gcacatcact cataatgatg gggtcadagg ttcgaatccc gtcgtagcca
      tRNA Met
651 ccaaattctg aatgtatcga atatgttcgg caaattcaaa accaatttgt
701 tggggtatcg ccaagcggta aggcaccgga ttCTAattcc ggcattccga
      tRNA Gln(CAG)
751 ggttcgaatc ctcgtacccc agccaattta ttcaagacgc ttaccttgta
801 agtgcaccca gttggggtat cgccaagcgg taaggcaccg gattctgatt
851 ccggcattcc gaggttcgaa tcctcgtacc ccagccacat taaaaaagct
      tRNA Gln (AAT)
901 cgcttcgggcg agctttttgc tttctgcgt tcattcaatg tcgaatgcga
951 tgttgacacg tcttatcctt caatgtcga tgcgacgctg ccgcgtctta
                                3'-CGCTGCGACGGCGCAGAATGCGCACGCG
                                           supE2-Mlu-lo
```

*Figure 6A*

```
CCGGGTCCGGAAGCGGTTCCGGG          TAACTGACTGACCCGCAG
|||||||||||||||||||||||          ||||||||||||||||||
CAGGCCTTCGCCAAGGCCC              ATTGACTGACTGGGCGTCCTAG
```

GCxxxxMRCKQDSDCLAGCVCqvlxpxxsxCG

| | | | | |
|---|---|---|---|---|
| 1GC | VMTG | IRCKQDSDCLAGCVCQVL | NPKTSN | CG |
| 3GC | VSSH | IRCKQDSDCLAGCVCQVL | HPPYQN | CG |
| 5GC | NRSL | IRCKQDSDCLAGCVCQVL | NPPTSN | CG |
| 7GC | MDTH | IRCKQDSDCLAGCVCQVL | NPPTSN | CG |
| 8GC | WERD | IRCKQDSDCLAGCVCQVL | HPSQSY | CG |
| 9GC | VTSL | IRCKQDSDCLAGCVCQVL | HPPYYN | CG |

MITHGCYTRT RHKHKLKKTL IMLSAGLGLF FYVNQNSFAN GENYFKLGSD 50
SKLLTHDSYQ NRLFYTLKTG ETVADLSKSQ DINLSTIWSL NKHLYSSESE 100
MMKAAPGQQI ILPLKKLPFE YSALPLLGSA PLVAAGGVAG HTNKLTKMSP 150
DVTKSNMTDD KALNYAAQQA ASLGSQLQSR SLNGDYAKDT ALGIAGNQAS 200
SQLQAWLQHY GTAEVNLQSG NNFDGSSLDF LLPFYDSEKM LAFGQVGARY 250
IDSRFTANLG AGQRFFLPAN MLGYNVFIDQ DFSGDNTRLG IGGEYWRDYF 300
KSSVNGYFRM SGWHESYNKK DYDERPANGF DIRFNGYLPS YPALGAKLIY 350
EQYYGDNVAL FNSDKLQSNP GAATVGVNYT PIPLVTMGID YRHGTGNEND 400
LLYSMQFRYQ FDKSWSQQIE PQYVNELRTL SGSRYDLVQR NNNIILEYKK 450
QDILSLNIPH DINGTEHSTQ KIQLIVKSKY GLDRIVWDDS ALRSQGGQIQ 500
HSGSQSAQDY QAILPAYVQG GSNIYKVTAR AYDRNGNSSN NVQLTITVLS 550
NGQVVDQVGV TDFTADKTSA KADNADTITY TATVKKNGVA QANVPVSFNI 600
VSGTATLGAN SAKTDANGKA TVTLKSSTPG QVVVSAKTAE MTSALNASAV 650
IFFDQTKAS

FIGURE 16B

MITHGCYTRT RHKHKLKKTL IMLSAGLGLF FYVNQNSFAN GENYFKLGSD 50
SKLLTHDSYQ NRLFYTLKTG ETVADLSKSQ DINLSTIWSL NKHLYSSESE 100
MMKAAPGQQI ILPLKKLPFE YSALPLLGSA PLVAAGGVAG HTNKLTKMSP 150
DVTKSNMTDD KALNYAAQQA ASLGSQLQSR SLNGDYAKDT ALGIAGNQAS 200
SQLQAWLQHY GTAEVNLQSG NNFDGSSLDF LLPFYDSEKM LAFGQVGARY 250
IDSRFTANLG AGQRFFLPAN MLGYNVFIDQ DFSGDNTRLG IGGEYWRDYF 300
KSSVNGYFRM SGWHESYNKK DYDERPANGF DIRFNGYLPS YPALGAKLIY 350
EQYYGDNVAL FNSDKLQSNP GAATVGVNYT PIPLVTMGID YRHGTGNEND 400
LLYSMQFRYQ FDKSWSQQIE PQYVNELRTL SGSRYDLVQR NNNIILEYKK 450
QDILSLNIPH DINGTEHSTQ KIQLIVKSKY GLDRIVWDDS ALRSQGGQIQ 500
HSGSQSAQDY QAILPAYVQG GSNIYKVTAR AYDRNGNSSN NVQLTITVLS 550
NGQVVDQVGV TDFTADKTSA KADNADTITY TATVKKNGVA QANVPVSFNI 600
VSGTATLGAN SAKTDANGKA TVTLKSSTPG QVVVSAKTAE MTSALNASAV 650
IFFDQTKASI TEIKADKTTA VANGKDAIKY TVKVMKNGQP VNNQSVTFST 700
NFGMFNGKSQ TQATTGNDGR ATITLTSSSA GKATVSATVS DGAEVKATEV 750
TFF

METHOD FOR EXPOSING PEPTIDES AND POLYPEPTIDES ON THE CELL SURFACE OF BACTERIA

The present invention concerns a method for exposing peptides, including polypeptides and proteins, depending on the length of the sequence exposed, on the surface of Gram-negative bacterial cells, especially *Escherichia coli* cells, an accompanying process for producing a variant population of surface-exposed peptides or polypeptides and for identifying bacteria which carry peptides or polypeptides with a particular desired property, and vectors and host bacteria which can be used in the process.

In general, the method allows expression of recombinant proteins, which can be receptors or ligands, on the bacterial surface and selection based on affinity of binding to a binding partner. The method allows expression of peptide and polypeptide libraries on the surface of bacterial cells, by means of which peptide molecules with high affinity to a ligand can be identified. The method allows exposure of a particularly large number of passenger proteins or peptides on the surface of a bacterial cell without adversely affecting its cellular viability. This method further allows setting the number of molecules presented on the surface of a cell as desired.

In particular, the present invention also concerns isolation of monospecific antibodies from polyclonal antibody mixtures by binding to peptide epitopes anchored to the cell surface.

BACKGROUND

Expression of proteins and protein domains on the surface of self-replicating carriers such as bacteriophages, bacteria, yeasts, etc., is currently under intense investigation. The primary objective is to achieve coupling of the functional expression of a property of the protein exposed on the surface of the carrier (phenotype) with the fundamental genetic coding (genotype). Examples of successful phenotype/genotype coupling appear, among others, in the use of yeasts as carriers of surface-exposed proteins. For instance, a molecular library of variant yeast cells is generated, each one of which has different immunoglobulin fragments exposed on its cell surface. Those cells which exhibit increased affinity to a specific ligand molecule can be isolated from that library of antibody variations (Boder and Wittrup (1997), Nat. Biotechnol. 15:1553).

Bacteria have broad applications for cell surface exposure. Both Gram-positive and Gram-negative types are used. For instance, proteins can be exposed on *Staphylococcus xylosus* and *Staphylococcus carnosus* by *Staphylococcus aureus* protein A. Enzymes can be anchored to the surface of *S. carnosus* by fusion to *Staphyloccus aureus* fibronectin binding protein B (FnBPB) (Strauss and Götz (1996), Mol. Microbiol. 21:491–500). However, Gram-positive bacteria are less suitable for exposure of large peptide libraries because it is difficult to introduce the corresponding gene variants into the cells by transformation and to generate a sufficiently large number of independent clones which differ with respect to the coding nucleotide sequence of the surface-exposed protein variants.

Gram-negative bacteria, on the other hand, are very well suited to generation of molecular libraries and to the accompanying exposure of altered proteins because of their high transformation yield (>10⁹ per microgram of plasmid DNA for *E. coli*), and so are preferred host organisms.

Various systems have been described for exposing recombinant proteins on the cell surface of Gram-negative bacteria (Georgiou et al. (1997), Nature Biotechnol. 15:29–34). In general, surface exposure is attained by fusing gene segments of a bacterial surface protein with the gene for the protein to be exposed. The proteins usually used as carriers are those which are secreted and/or localized in the external membrane of Gram-negative bacteria and therefore contain the signals needed for translocation through the cytoplasmic membrane, passage into the bacterial periplasm, and integration into the external membrane or anchoring on the surface of the external membrane. The carrier proteins that have been used most are those which are themselves integral components of the external membrane of *E. coli*. Those include, among others, PhoE (Agterbert et al. (1987), Gene 59:145–150) or OmpA (Francisco et al. (1992), Proc. Natl. Acad. Sci. USA 89:2713–2717); but there are disadvantages to their use. For instance, protein sequences can be inserted only into surface-exposed loops of these proteins. That results in conformationally fixed amino and carboxy terminations, and drastically limits the length of the peptide sequence to be inserted. Use of the peptidoglycan-associated lipoprotein (PAL) as a carrier protein does indeed result in transport to the external membrane, but it is impossible to expose active and correctly folded protein sequences on the surface of *E. coli* (Fuchs et al. (1991), Bio. Technology 9, 1369–1372). It has been possible to expose large proteins on the surface by (a) use of fusion of a fragment of the *Escherichia coli* Lpp and of the OmpA protein as the carrier protein portion, to the carboxy end of which the passenger protein sequence is attached (Francisco et al. (1992), Proc. Natl. Acad. Sci. 89:2713–2717); (b) use of the IgA protease (domain (IgAβ) and other bacterial autotransporters (Maurer et al. (1997) J. Bacteriol. 179: 794–804), and (c) by use of the ice nucleation protein of *Pseudomonas syringae* (InaZ) (Jung et al. (1998), Nature Biotechnol. 16:576–580 as the carrier protein portion.

It is clear from the examples above that proteins can be exposed on the bacterial cell surface by joining a passenger domain to a carrier protein by fusion of the corresponding coding DNA sequence with the coding sequence of a selected protein of the external membrane or membrane protein fragment. In this case the membrane protein or membrane protein fragment provides the force needed for the membrane localization and anchoring. Here the carrier protein of the external membrane should (a) have a secretion signal that assures passage through the cytoplasmic membrane; (b) exhibit a localization signal for embedment into the external membrane; (c) appear on the cell surface in the highest possible number of copies; and (d) not have a negative effect on the structural and functional integrity and, in particular, the vitality of the host cell.

Substantial problems have been found, though, with the processes described at the state of the art for production of heterologous passenger proteins using proteins of the external membrane, particularly with respect to requirements (c) and (d). A high expression ratio and a high net accumulation in the external membrane are always accompanied by high mortality of the bacterial cells which expose them. For instance, strong over-expression of fusion proteins with Lpp-OmpA as the membrane anchor is lethal (Daugherty et al. (1999), Protein Eng. 12:613–21). High cell mortality was likewise described for use of the autotranporter of the IgA protease (IgAβ) (Wentzel et al. (1999), J. Biol. Chem. 274: 21037–21043). Jung et al. Introduced the ice nucleation protein of *Pseudomonas syringae,* which is a glycosyl-phosphatidylinositol anchored protein of the external membrane, into *E. coli* as a carrier protein for cell surface exposure of passenger proteins (Jung et al. (1998), Nature Biotechnol. 16: 576–580). This carrier protein does allow stable exposure of passengers on the surface of the external membrane; but the fusion proteins aggregate in clusters on the bacterial surface. That characteristic is undesirable for the purpose of selecting peptides and polypeptides with high affinity to a specific binding partner.

Aside from the proteins integral to the external membrane, other surface structures present on the cell surface, such as flagellae, pili, fimbriae, etc., have been used as carriers for exposure of passenger domains. Various peptides of Hepatitis B virus were stably expressed and exposed on the bacterial surface by use of flagellin, a subunit of the flagellum, as the carrier (Newton et al. (1989), Science 244: 70–72). However, as for use of fimbrin as a structural carrier protein, exposure of passenger domains remains limited to small peptides (Hedegaard et al. (1989), Gene 85: 115–124).

Technical Problems, and Their Solution by the Present Invention

The present invention is, therefore, based on the technical problem of providing carrier proteins, which do not result in the disadvantages stated above, especially with use of *Escherichia coli*.

An optimal presentation procedure must meet the following requirements:
1. The peptide/protein to be exposed should preferably be anchored on the surface of a bacterial cell in the highest possible number of copies.
2. The peptide/protein exposure should not impair viability.
3. The number of peptide/protein molecules exposed on the surface per cell should be controllable within wide limits.

No method of bacterial surface exposure which meets these requirements in all points has yet been described.

SUMMARY OF THE INVENTION

To achieve the objective stated above, a process is provided for exposure of peptides and/or polypeptides on the surface of host bacteria in which one (a) produces a Gram-negative host bacterium which is transformed with a vector to which is localized a fused nucleic acid sequence that (i) has a sequence segment that codes for an Intimin shortened by at least the C3 domain at the carboxy terminus region as the anchoring domain and (ii) has a nucleic acid segment coding for the passenger peptide and/or passenger polypeptide to be exposed, and (b)

cultivates the host bacterium under conditions in which the coded nucleic acid sequence is expressed and the peptide or polypeptide coded by the nucleic acid sequence (ii) is exposed on the surface of the host bacterium, such that the nucleic acid sequence (ii) is heterologous with respect to the nucleic acid sequence segment coding for the Intimin membrane anchoring domain.

The shortened Intimin can be shorted by at least one more of the domains D0, D1 and/or D2 in the carboxyterminal region of 280 amino acids (aside from the shortening by the D3 domain).

The method of the invention allows exposure of peptides or polypeptides on the surface of Gram-negative host bacteria using certain Intimin-based anchoring modules. It has been found that Intimins shortened at the carboxy terminus are particularly well suited as anchoring units in the external *E. coli* cell membrane for passenger domains.

The invention is based on providing a gene construct in which a special carrier protein (a fragment of the "Intimin", see below) is used as the exposure anchor. To expose a specified peptide/protein, the coding gene is fused to the coding sequence of the Intimin gene fragment in the continuous reading frame. Surprisingly, it is found that when an Intimin fragment is used as the membrane anchor a very large number of molecules can be exposed in the bacterial membrane without impairing the viability of the host bacteria.

(b) [sic/tr. note #1] We have succeeded in establishing the number of molecules per cell as we wish by combined regulation of the expression of the Intimin gene at the transcription and translation level. Processes previously described for regulating gene expression for the purpose of establishing surface-exposed molecules do not do that.

Intimin as the Exposure Anchor

The further development of the invention provides that the Intimin anchoring domain in the external bacterial membrane be derived from the genus of the Enterobacteriaceae and used in a host bacterium of a genus of the Enterobacteriaceae [sic/tr. Note #2]. It is further preferable for the anchoring domain to be a fragment of the Intimin of enterohemorrhagic *E.coli* or a variant of it. At present a carboxy-terminal shortened variant of the BacA Intimin from enterohemorrhagic *Escherichia coli* O157:H7 comprising amino acids 1 to 659 (see FIG. 16A, SEQ ID NO: 25) or, alternatively, amino acids 1 to 753 (see FIG. 16B. SEQ ID NO: 26), is particularly preferred.

Many strains of pathogenic bacteria have surface structures such as pili, glycoproteins and other proteins, such as homopolymeric and heteropolymeric carbohydrate glycocalices, by means of which the bacteria adhere to surfaces of eucaryotic cells. Proteins of the bacterial cell surface called Intimins play an important part in the firm adhesion of enteropathogenic (EPEC) or enterohemorrhagic *E. coli* (EHEC) bacteria to the surfaces of eucaryotic host cells. The Intimin-mediated adhesion allows the bacteria to multiply on the surfaces of the colonized host cells. Intimin is a member of the family of bacterial adhesion molecules which have sequence homologies with each other in the area of the amino-terminal region (McGraw et al. (1999), Mol. Biol. Evol. 16:12–22).

Intimin is the product of the Eae gene. It has 939 amino acid groups. Its cell-binding activity is localized in the 280 C-terminal amino acid groups. Intimin is anchored in the external membrane with its amino-terminal domain, which exposes the 280 carboxy-terminal amino acids. These 280 groups code for three domains, two immunoglobulin-like domains and one lectin-like domain (Kelly et al. (1999), Nat. Struct. Biol. 6:313–318) code for these 280 groups, which are responsible for binding to eucaryotic cells. The structures of domains D1, D2 and D3 are known, but not the structure of the amino-terminal domain (Kelly et al. (1999) Nat. Struct. Biol. 6:313–318). FIG. 1 shows the schematic structure of Intimin and its anchoring in the external membrane. Corresponding domains of other Intimins can be derived from sequence comparisons.

Except for the 200 amino-terminal amino acid groups, Intimins exhibit sequence homologies with invasins from *Yersinia* and other bacteria which make it possible for the bacterium to enter cultivated mammalian cells through binding with integrins (Leong et al. (1990), EMBO J. 9:1979–1989). Integrins and invasins do, to be sure, have similar sequences, but they are assigned to different protein families with respect to their functions (Batchelor et al. (2000), EMBO J. 19:2452–2464).

Surprisingly, surface presentation of peptides or polypeptides distinctly improved over the state of the art was attained by use of a fragment of *Escherichia coli* Intimin as the transporter domain for bacterial surface localization of passenger proteins and passenger peptides, particularly also of short synthetic peptides having lengths of preferably 6 to 20 amino acids, by disulfide-bridged peptides and polypeptides, especially oligopeptides on the structural basis of the cystine node folding motif (Pallaghy et al. (1994), Protein Sci. 3: 1833–1839), or by bacterial (e. g.: (-lactamase inhibitor protein) and eucaryotic polypeptides (e. g., interleukin 4).

Identification of Eae Intimin as the Carrier Protein for Surface Exposure of Passenger Proteins The *Escherichia coli* Intimin that is used preferably is localized in the external membrane of *Escherichia coli*. It naturally exposes at least one protein domain on the outer side of the external membrane. The *Escherichia coli* Intimin is anchored in the external membrane, and carries at its carboxy-terminal end four domains which are necessary for interaction with a receptor protein on the surface of epithelial cells.

Beginning with the working hypothesis that substitution of at least one of the Intimin domains exposed on the cell surface by a heterologous passenger domain would result in that domain being exposed on the surface, a gene fusion was produced from a nucleic acid segment coding for a passenger protein and one coding for an Intimin fragment. Example 1 presents the gene fusion from the Intimin fragment and the passenger domain, the vector construction, and the expression in host bacteria, compared with other surface presentation methods.

In general, the Intimin gene or gene fragment selected for gene fusion is amplified by the polymerase chain reaction and cloned in a vector suitable for expression in the intended host bacterium. A gene for a passenger peptide to be exposed is introduced into the same gene downstream from the selected Intimin fragment in the same reading frame. The vector also contains an exogenously inducible promoter operatively linked with the Intimin gene and with the passenger peptide fused with it. Other functional sequences, such as marker genes, can also be present.

In further development of the invention, the process is arranged so that the expression of the fusion gene from the nucleic acid sequence segment coding for the shortened Intimin and for the passenger protein can be regulated by (i) replacing a codon coding for a glutamine in the shortened nucleic acid sequence segment coding for the shortened Intimin by an amber stop codon (TAG), and (ii) using an *Escherichia coli* host strain in which a translation of the mRNA of the fusion gene is accomplished by providing a controllable quantity of suppressor tRNA, which allows over-reading of the stop codon on translation. This procedure allows effective regulation of the expression of the segment exposed within the host cell, and is useful for practically all known exposure processes.

In the further developed process a CAG codon within the Intimin fragment is replaced by a TAG stop codon. That is accomplished, for instance, by cloning a PCR fragment in which the CAG codon #35 in the Intimin is replaced by a TAG stop codon. By use of an amber suppressor strain, this stop codon is over-read and a glutamine group is incorporated at this position. As the efficiency of amber suppression is low, fewer molecules are synthesized than in the absence of the stop codon. The result is that the number of surface-exposed molecules remains within an extent that is tolerable for the cell (in this connection, see Christmann et al. (1999), Protein Eng. 12: 797–806). Any expression vector particularly usable for expression in *E. coli* can be used. The vector pASK75 (see below), among others, is a suitable starting vector.

Regulation of the Gene Expression

Expression of a gene is usually regulated by the coding sequence of a gene being brought under control of a promoter such that the number of transcriptions per unit time can be regulated by the concentration of an inducer molecule added exogenously. For instance, the lac promoter, the ara promoter, or the tetA promoter can be considered for that purpose (Lutz & Bujard (1997), Nucleic Acids. Res. 25:1203). It has not previously been possible satisfactorily to regulate gene expression with the goal of establishing a desired number of surface-exposed molecules per bacterial cell by controlled induction of the transcription of the gene for surface-exposed fusion proteins. Variation of the concentration of an added inducer has not previously resulted in accumulation of fusion proteins on the surface of the bacterial cell depending on the concentration of the inducer (Daugherty et al. (1999), Protein Eng. 12: 613–621). A slight improvement was gained by adjusting the net accumulation by means of the induction period. That means that the transcription inducer was added to a bacterial culture, and the cells were incubated with the inducer for different times. The longer the induction time, the higher the number of surface-exposed cells per cell [sic/tr. note #5]. This process is not suitable for highly parallel biotechnological applications, as it requires sample collection at different growth times. Also, the cells are in different physiological states, depending on the growth time and the absorbance [sic/tr. note #7] attained.

The process which we have developed eliminates this disadvantage. The gene expression is controlled on two levels, the level of transcription and the level of translation.

In one process according to the invention, fusion proteins are produced by replacing a codon coding for glutamine (CAG) in the nucleic acid sequence coding for the Intimin or Intimin fragment by a amber stop codon (TAG). This codon is preferably the first glutamine codon of the amino acid sequence of Intimin or the Intimin fragment. Likewise, a different codon within the first 100 amino acids of the Intimin or Intimin fragment can be replaced by TAG. Now a modified *E. coli* strain is offered in trans a modified glutaminyl-tRNA, which carries the genetic marker supE. This supE tRNA is able to pair in the translation with a TAG codon, and to cause suppression of the translation stop.

An *E. coli* host bacterium which contains the nucleic acid sequence segment coding for the supE gene in operative linkage with a controllable promoter is according to the invention. The PI lac promoter, with which the intensity of expression and thus the rate of synthesis of supE transfer RNA can be controlled by the amount of the inducer IPTG added to the growth medium for the host bacteria, is preferred. In one typical example, the nucleic acid sequence segment, which codes for a supE tRNA gene in operative linkage with a controllable promoter is localized in a vector compatible with the expression vector. Transcription of the gene for the Intimin passenger domain fusion protein is switched on by addition of an inducer (anhydrotetracycline in this case). Different, and freely adjustable, quantities of suppressor tRNA for synthesis of the Intimin fusion protein are made available in the cell by varying the amount of IPTG inducer. Finally, the amount of supE tRNA determines the average number of passenger domains exposed on the surface of a bacterial cell. FIG. 5 shows schematically the newly developed expression process.

Embodiments

The process according to the invention produces a host bacterium transformed with one or more compatible vectors. Such a vector contains a fused nucleic acid sequence in operative linkage with a promoter and optionally other sequences needed for the expression. This fused nucleic acid sequence includes (a) a nucleic acid sequence segment coding for an Intimin fragment which makes possible exposure of the peptide or polypeptide coded by segment (b) on the outside of the external membrane of the host bacterium and (b) a nucleic acid sequence segment coding for the protein and/or peptide to be exposed.

In one preferred embodiment, then, the present invention concerns an Intimin, a fragment of Intimin, or a carrier protein homologous with Intimin, which exerts a transporter function and allows surface exposure of recombinant proteins in the host bacteria in high numbers of copies. This involves the amino-terminal fragment of the Eae Intimin from enterohemorrhagic *Escherichia coli* Serotype O157: H7 (Louie et al. (1993), 61:4085–4092) which extends from amino acid 1 to 659. Along with this specific sequence, the invention also covers use of variants, which can, for example, be produced by alteration or deletion in the amino acid sequence in the sequence segments not essential for translocation through the cytoplasmic membrane and localization in the external membrane.

Another typical example involves gamma Intimin from *E. coli* (Gene Bank Accession Number AF081182), Intimin from *E. coli* O111 :H— (Gene Bank Accession Number AAC69247) or Intimin from other *Escherichia coli* serotypes or the Intimin from Citrobacter freundii (Gene Bank Accession Number AAA23097) as the transporter protein used. The DNA sequences and the amino acid sequences derived from them for the Intimins listed above can be found as NCBI citations (National Center for Biotechnology Information, USA) at the locations listed below.

Other Intimin domains can be derived from protein sequences in databases, from protein sequences based on DNA sequences available in databases, or from protein sequences determined by sequence analysis directly or indirectly from the DNA sequence. The corresponding coding regions (genes) can be used to produce vectors or fusion protein genes, which make possible effective surface expression of passenger proteins in Gram-negative bacteria, especially *Escherichia coli*.

In the invention, surface presentation or exposure means that the fusion proteins or passenger domains are localized on the side of the external bacterial membrane toward the medium. Surface-exposed passenger proteins in intact Gram-negative bacteria are freely accessible for binding partners.

In one preferred embodiment, the present invention thus enables surface exposure of peptides or, in a further embodiment, the surface exposure of peptide libraries in Gram-negative bacteria, especially in *E. coli*, and their use to determine affinity to an antibody or another receptor.

In another preferred embodiment, the present invention makes possible mapping of epitopes and isolation of monospecific antibodies from an antibody mixture. Epitope mapping means that the peptide with the highest affinity to an antibody or another receptor, exposed on the surface of the producing strain, is identified. That makes clear a critical advantage of the present invention for expression of peptide libraries, compared with the phage systems used for such applications (Makowski (1993), Gene 128: 5–11; Kuwabara et al. (1997), Nat. Biotechnol. 15: 74–78). In the bacterial system according to the invention, selection of the clonal producers occurs simultaneously with identification of a peptide having the desired binding property. They can be multiplied immediately. In one typical example, clonal descendants of the producers were used to purify or isolate an antibody or another receptor from a mixture of molecules. That occurs through binding of the receptor molecules with high affinity to the peptide molecules exposed on the bacterial surface, followed by separation of the unbound molecules by centrifugation and/or filtration, and separation of the monospecific antibodies or receptor molecules from the surface-exposed peptides.

Multiplication of the strain expressing the desired surface-exposed peptide or protein accomplishes amplification of the corresponding coding gene. Sequence analysis of that gene allows unambiguous and simple identification and characterization of the peptide or protein. Thus a peptide library prepared in that manner contains fusion proteins, made up of an Intimin or an Intimin fragment and a peptide or protein produced and surface-exposed in a Gram-negative bacterium, preferably *E. coli*. In one typical example, cloning of synthetic oligonucleotides degenerated at selected positions behind the coding sequence of Intimin or Intimin fragments achieves the high variance of the different expressed proteins.

In one particularly preferred embodiment, the process according to the invention makes possible surface expression and variation of a peptide or polypeptide having an affinity to a binding partner, a ligand, a receptor, an antigen, a protein with enzymatic activity, an antibody, or an antigen-binding domain of an antibody.

The process according to the invention for producing a variant population of surface-exposed peptides and for identification of bacteria, which carry the peptides or polypeptides with a desired property, is organized in the following steps:

1) Production of at least one fusion gene by cloning the coding sequence of a desired passenger in the continuous reading frame downstream from an Intimin gene or an Intimin gene fragment in at least one vector.
2) Variation of the passenger by cloning passengers from a gene mixture, or through site-directed mutagenesis, e.g., by the polymerase chain reaction (PCR) using oligonucleotides with deliberately replaced bases, by random mutagenesis using oligonucleotide mixtures with randomly produced base sequences in selected sequence segments in the PCR, by error-prone PCR, by randomly controlled chemical mutagenesis, or by use of high-energy radiation.
3) Incorporation of the vector or vectors in host bacteria.
4) Expression of the fusion gene in the host bacteria, which then express the fusion protein stably on their surfaces.
5) Cultivation of the bacteria in liquid culture or on agar plates for clonal expansion.
6) Optional selection of the bacteria which carry the passenger with the desired properties, and
7) Optional characterization of the selected passenger through sequencing of the nucleic acid sequence segment coding the passenger peptide or polypeptide.
8) Optional isolation and purification of a binding partner for the passenger with the optimal properties.

This process can be carried out repetitively.

In one preferred embodiment of this process, the bacteria having a stable exposed fusion protein with the desired properties are isolated by binding to an immobilized and/or labeled binding partner, e. g., a matrix-fixed binding partner, a magnetic-particle-labeled binding partner, or a chromogenically or fluorogenically labeled binding partner.

Bacterial Surface Exposure of Protein Fragments, Epitope Mapping and Isolation of Monospecific Antibodies.

Every protein carries many antigenic determinants on its surface. As a result, the immune response to such a molecule is always stimulation of many B-lymphocytes and production of just as many antibody species. Knowledge of the amino acid sequence of such epitopes is of great importance for immunological research.

It would be advantageous for many applications if one could obtain large amounts of monospecific antibodies from mapped serum immediately after mapping of epitopes. Monospecific antibodies are equally monoclonal in their properties, and are also sold commercially. To isolate such antibodies, the peptides, which comprise the epitope, must be coupled to a matrix. Then the serum is passed over that matrix, and the antibodies, which bind specifically to the desired antigen, are eluted. In this example of the application of the Intimin-based bacterial surface exposure, epitope-presenting E. coli cells were used as such a matrix.

FIG. 9 shows a survey of the procedure in epitope mapping using Intimin-mediated cell surface exposure. Example 2 presents the use of this process.

Isolation of Peptides with Affinity to a Specific Target Protein Through Intimin-based Surface Exposure of Combinatory Peptide Libraries To check whether Intimin-based bacterial surface exposure is suitable for isolating from a molecular collection of surface-exposed peptide variants those which have affinity to a specified target protein, a library of variants of the cystine node protein EETI-II, comprising 28 amino acids, was generated. EETI-II is an inhibitor of trypsin proteases which occurs in the vegetable marrow *Ecballium elaterium*. This peptide is stabilized by three intramolecular disulfide bridged which spread out a group of surface loops (described in Wentzel et al. (1999), J. Biol. Chem. 274: 21037–21043). A library of EETI-II variants was generated, in which the residues of two loop regions exposed to the solvent are randomized. Example 3 presents the experimental procedure for this example embodiment.

The invention is explained in more detail in the following using some experimental examples which will make it easier to understand the invention, but which are not intended to limit the invention to these examples. Those skilled in the art will recognize which alternatives are possible within the outlines of the invention on the basis of these examples.

BRIEF DESCRIPTION OF THE FIGURES

The accompanying figures will serve for further explanation of the invention. Individually, they show:

FIG. 6a: Nucleotide sequence and genetic organization of the sequence segment of the E. coli genome fromBMH71-18 (SEQ ID NO:16) amplified by the PCR primers SupE2-Eco-up (SEQ ID NO: 10) and SupE2-Mlu-lo (SEQ ID NO:11, complement). The tRNA coded genes are emphasized in bold type.

A) Unselected library labeled with anti-β-lactamase serum, anti-rabbit antibodies (biotin conjugate) and streptavidin-R phycoerythrin. 1.6% of the cells appear in the window used (fluorescence channels 300–1024). B) Second round of sorting (labeling as in A); C) Third round (labeling as in A).

FIG. 15: Amino acid sequence of the 6 EETI variants (1, 3, 5, 7, 8 and 9), which interact with the anti-β-lactamase antibodies; randomized amino acids are underlaid with gray.

Underlines indicate a mutation from the wild type gene in the DNA sequence. A consensus sequence for binding to the anti-underlaid with gray. Underlines indicate a mutation from the wild type gene in the DNA sequence. A consensus sequence for binding to the anti-β-lactamase antibody is shown for the rear loop region. Variant 1, SEQ ID NO: 1; Variant 3, SEQ ID NO: 5; Variant 5, SEQ ID NO: 2; Variant 7, SEQ ID NO: 16 Variant 8, SEQ ID NO: 3; Variant 9, SEQ ID NO: 4.

FIG. 16A and B. A, sequence of amino acids 1 to 659 from enterohemorrhagic *Escherichia coli* O157:H7 (SEQ ID NO: 25); B, sequence of amino acids 1 to 753 from enterohemorrhagic *Escherichia coli* O157:H7 (SEQ ID NO: 26).

EXAMPLES

Example 1

Figure 6B:
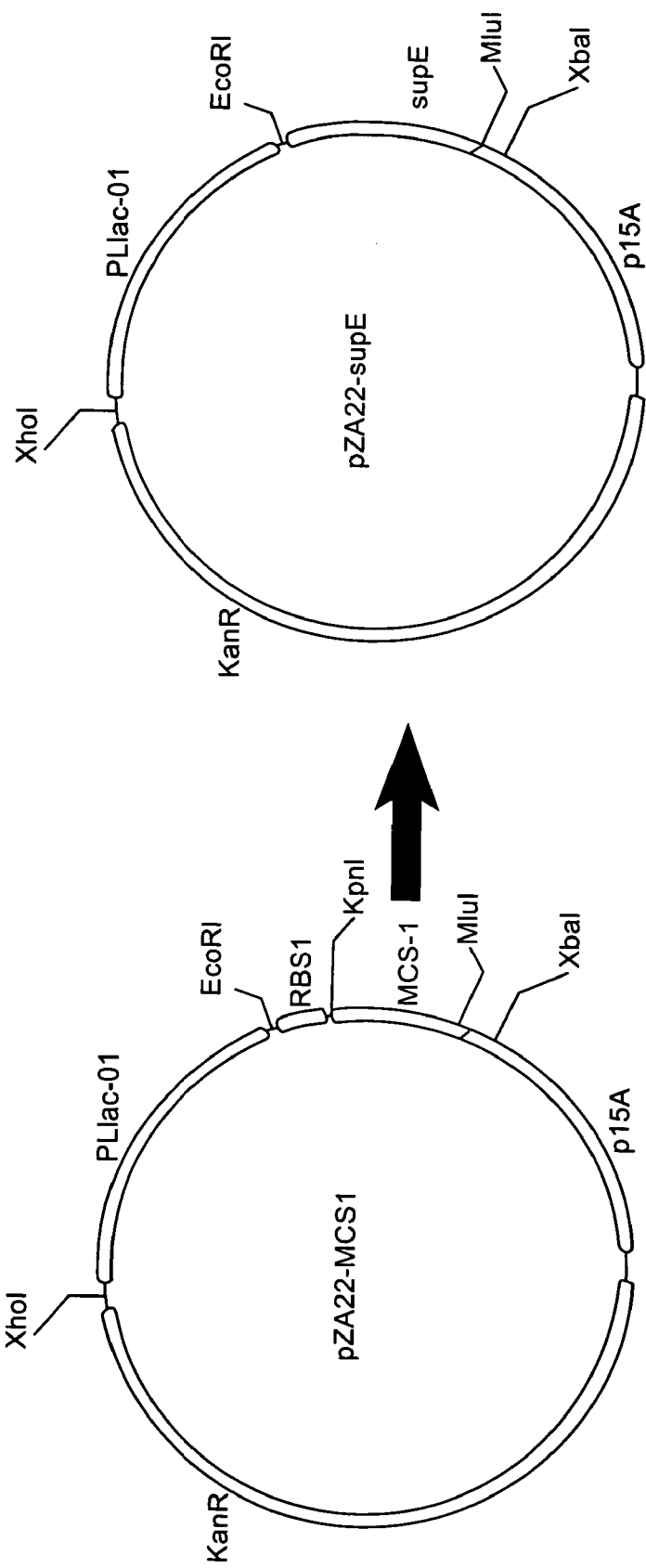
FIG. 6b: Schematic representation of the vector pZA22-MCS1 (Lutz & Bujard (1997), Nucleic Acids Res. 25:1203) and of the vector pZA22-supE resulting from incorporation of the supE gene. PL-lac-O1: hybrid operator/promoter region from the PL operator and the lac promoter; RBS: ribosomal binding site; MCS-1: polylinker sequence; P15A: replication origin; KanR: Kanamycin resistance gene.

Gene Fusion of a Nucleic Acid Sequence Segment Coding for a Passenger Protein and One Coding for an Intimin Fragment Vector Construction, and comparative Example The cystine node polypeptide EETI-II, a trypsin protease inhibitor comprising 28 amino acids, was selected as the passenger for the first example (as previously used by: Wentzel et al. (1999), J. Biol. Chem. 274: 21037–21043; Christmann et al. (1999), Protein Eng. 12: 797–806).

For that purpose, the Intimin gene eae (Gene Bank Accession Z11541) from EHEC O157:H7 Strain 933 bacteria was amplified with the polymerase chain reaction using the oligonucleotides Intiminup (SEQ ID NO:9) and Intiminlo (SEQ ID NO:8). EHEC O157:H7 bacteria inactivated by boiling were used as the template. The gene was amplified with the following amplification conditions: 30 sec 94° C., 30 sec 53° C. and 2 min 72° C., 30 cycles.

The oligonucleotide Intiminup hybridizes the eae gene from nucleotide 69 to 88. This sequence segment contains the ATG start codon and the 17 nucleotides downstream from it. This oligonucleotide contains 5' additional sequences which [represent/tr. note #6] cloning of the PCR product on the 5' side into the XbaI cleavage site of the vector pASK21TE-EETI-CKSend (Christmann et al. (1999), Protein Eng. 12: 797–806). The oligonucleotide Intilo1 hybridizes the eae gene from nucleotide 2028 to 2045 and contains at the 5'end the coding sequence for a MluI cleavage site which allows cloning at the 3' end in the EcoRI cleavage site of vector pAsk21-EETI. Thus the PCR product contains the coding nucleic acid sequence for codons 1 to 659 of the Intimin. Then a tripartite fusion gene in operative linkage with the tetA promoter/operator is localized in the resulting vector pASK-Inti-EETI. It consists of (a) the coding nucleic acid sequence for Intimin from Codon 1 to 659; (b) the coding nucleic acid sequence for an epitope from the human Gla protein comprising 17 amino acids (Etag; Kiefer et al. (1990), Nucleic Acids res. 18: 1909) and (c) the coding nucleic acid sequence for the cystine node polypeptide EETI-CKSend (Christmann et al. (1999), Protein Eng. 12: 797–806; FIG. 2).

By cloning a PCR fragment, the CAG codon number 35 in Intimin was replaced by a TAG stop codon.

A second plasmid (pASK21TE-EETI-CKSend) in which the Intimin sequence is replaced by a shortened OmpA fragment (Christmann et al. (1999), Protein Eng. 12:797–806) was used to be able to compare the expression level with previous processes for surface exposure.

The strain BMH71-18 (Christmann et al. (1999), Protein Eng. 12: 797–806) was used as the bacterial strain for the gene expression.

BMH71-18: [$F^1$laol$^q$ lacZΔM15, proA+B+; Δ(lao-proAB), supE, thi]

The transformed cells were grown at 37° C. to an absorbance of 0.2 to 0.4. Expression of the fusion gene was induced by addition of 0.2 ug/ml anhydrotetracycline. The surface exposure was demonstrated by binding of a monoclonal anti-Etag antibody to the surface of the cells by means of indirect fluorescence labeling. That was done by centrifuging the cells off after one hour of incubation and incubating them successively with monoclonal anti-Etag antibody, biotinylated anti-mouse antibody and streptavidin, phycoerythrin conjugate exactly as described by Christmann et al., (1999), Protein Eng. 12: 797–806. The labeled cells were measured in a flow cytometer (FIG. 3). The FACS diagram shows the fluorescence of cells which produce no fusion protein (negative control, A), those which produce the Intimin-Etag-EETI fusion protein (B) and, for comparison, (C) cells transformed with a plasmid in which the Intimin membrane anchor has been replaced by an Ipp-OmpA membrane anchor corresponding to the previous Sder technique.

As can be seen from this figure, the cells in which Intimin-mediated exposure of the fusion partner occurs exhibit about ten-fold higher fluorescence than the cells with the usual membrane anchor. This finding shows, surprisingly, that there are about ten times more molecules of the passenger protein available on the bacterial surface when the Intimin membrane anchor is used. Furthermore, the viability of the cells, which is strongly reduced in the previously described processes for over-expression of membrane-anchored passenger proteins, is not notably impaired by the overproduction of the fusion protein from the Intimin fragment and the passenger domain. The survival proportions of the cells before and 1, 2 and 4 hours after induction of the expression of the fusion protein is shown below (FIG. 4).

Combined Use of supE tRNA in Host Organisms and the Amber Stop Codon in the Intimin Fragment The CAG codon number 35 in Intimin was replaced with a TAG stop codon by cloning a PCR fragment. When an amber suppressor strain is used, this stop codon is over-read and a glutamine is incorporated at that position. As the efficiency of the amber suppression is low, fewer molecules are synthesized than in the absence of the stop codon. That makes sure that the number of surface-exposed molecules remains within an extent that is tolerable for the cell (in this respect, see Christmann et al. (1999), Protein Eng. 12: 797–806). FIG. 2 shows the nucleotide sequence of the 5'-terminal and the '3' terminal part of the Intimin gene in the expression vector pASK-INT-EETI-CKSend, with the amber stop codon #35 emphasized in bold face.

The amber suppressor strain BMH71-18 was used as the PCR template to obtain the supE.

BMH71-18: [$F^1$ laol$^q$ lacZΔM15, proA+B+; Δ(lao-proAB), supE, thi]

The gene was amplified from the genome under standard conditions using the primers SupE2-Eco-up (SEQ ID NO:10) and SupE2-Mlu-lo (SEQ ID NO:11). FIG. 6*a* shows the sequence of the genome segment and of the primer.

On page 15, please amend the fourth full paragraph as follows:

The two PCR primers SupE2-Eco-up (SEQ ID NO:10) and SupE2-Mlu-lo (SEQ ID NO:11) were used for amplification. The supE gene lies in a cluster of tRNA genes, which are transcribed polycistronically and then processed and liberated by specific RNAses. The supE gene and at least one additional tRNA gene upstream and downstream were amplified with these oligonucleotides. The primers also introduce an EcoRI- and a MluI cleavage site. The resulting DNA segment was hydrolyzed with EcoRI and MluI and placed in the vector PZA22-MCS1 split with EcoRI and MluI (Lutz & Bujard (1997), Nucleic Acids Res. 25:1203), as shown in FIG. 6b.

Figure 7:
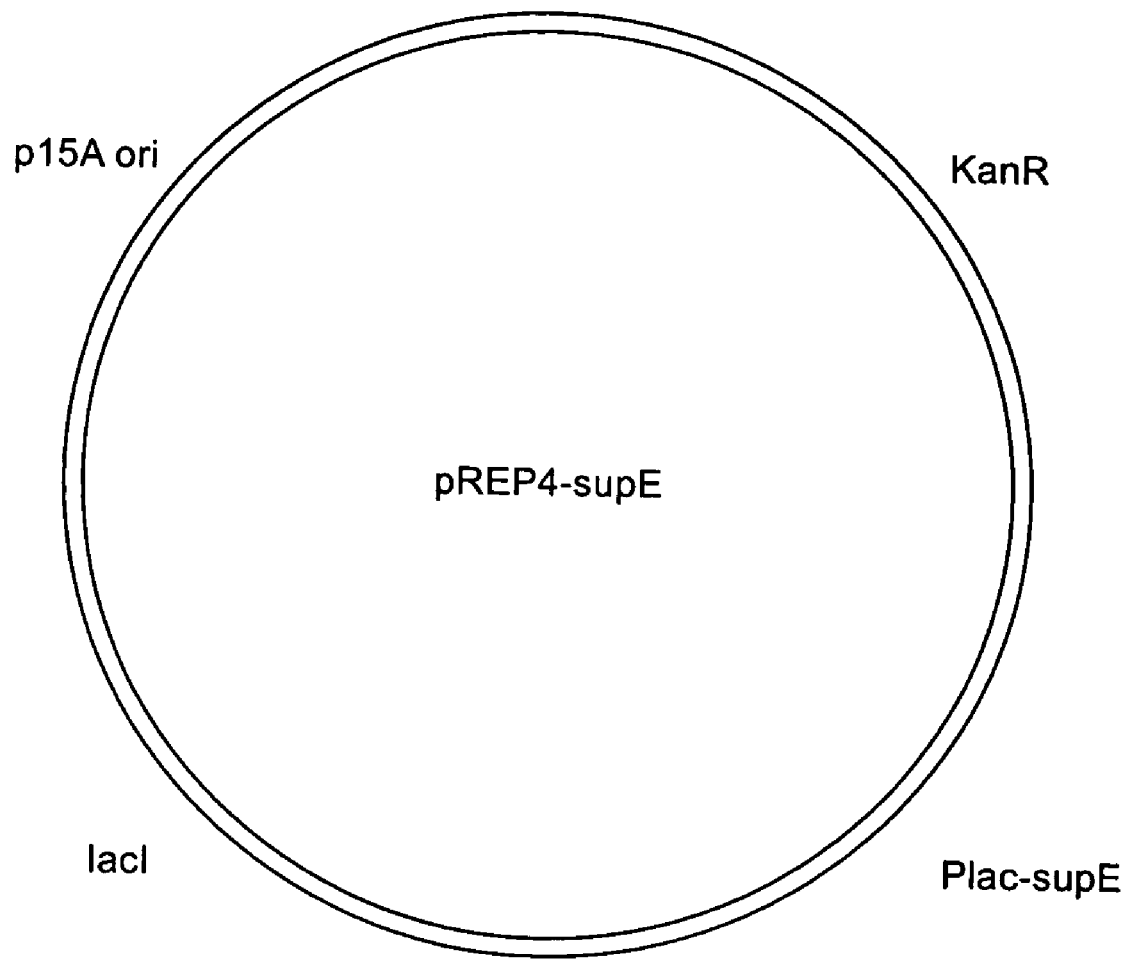
FIG. 7: Schematic representation of the vector pREP4-supE. Plac-supE: hybrid operator/promoter region of the PL operator and the lac promoter (Lutz & Bujard (1997) Nucleic Acids Res. 25:1203) followed by a sequence segment containing the supE gene. P15A: replication origin; KanR: kanamycin resistance gene; lacI: gene for the lac repressor.

The sequence segment coding for the supE gene appears in this vector, again under the control of the P<lacO-1 promoter/operator MCS1 (Lutz & Bujard, Nucleic Acids Res. 1997, 25:1203) inducible with IPTG. The promoter/operator and the supE gene sequence segment downstream from it were removed by splitting the resulting plasmid with XhoI and XabI. The ends were filled out with T4 polymerase in the presence of dATP, dGTP, dCTP and dTTP. The resulting fragment was inserted into the vector pRep4, split with SmaI (Qiagen). FIG. 7 shows a schematic map of the resulting vector.

Figure 8:
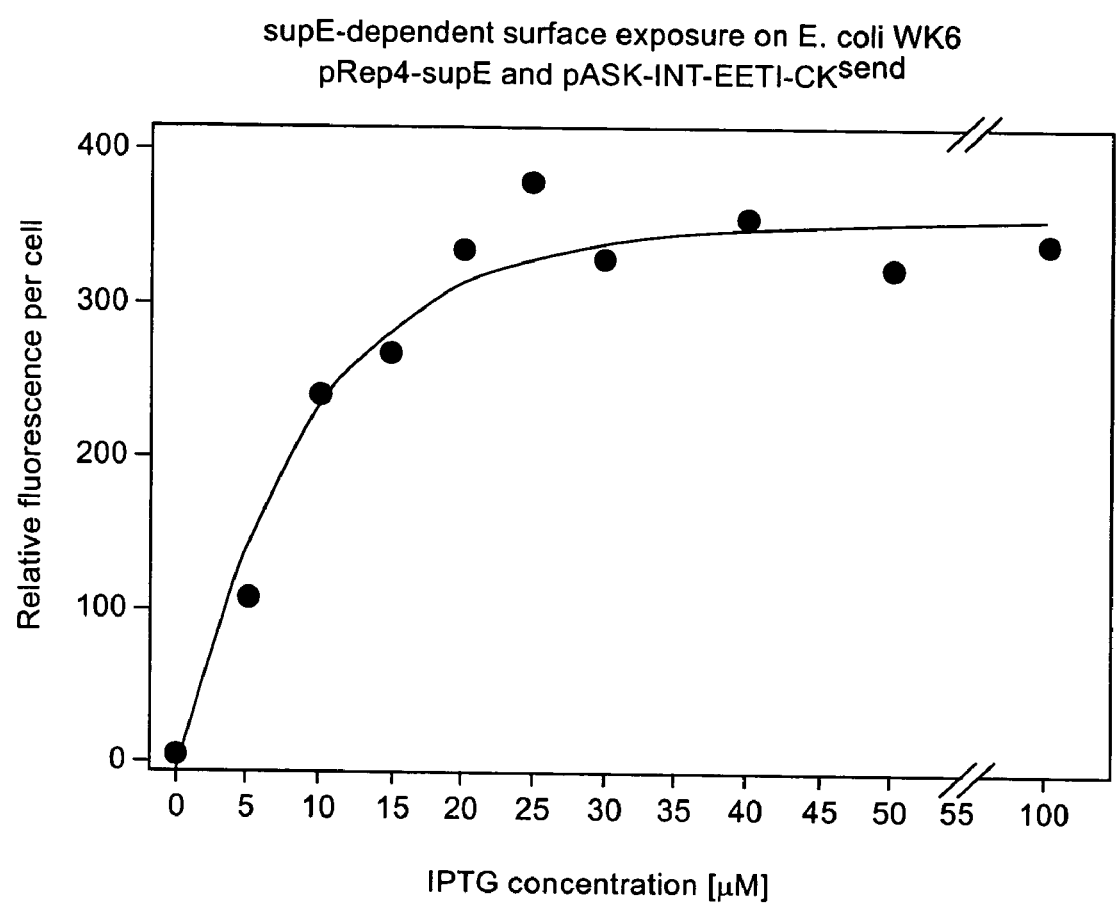
FIG. 8: Regulation of the synthesis and surface exposure of Intimin-anchored passenger domains by controlled provision of supE-tRNA.

Transcription of the supE gene from pREP4-supE can be induced by IPTG induction, thus inducing formation of supE-tRNA, which can be controlled by varying the quantity of the inducer. The plasmid pREP4-supE was incorporated into the E. coli strain WK6 [(lac-proAB), thi, rpsL, nal$^r$; F$^1$lacI$^4$, lacZM15, proA+B+] to demonstrate ability to control expression of surface-exposed proteins. This strain has no chromosomally coded supE gene. The strain was also transformed with the expression plasmid pASK-INT-EETI-CKSend (see above). The E. coli strain, now transformed with two plasmids, was cultured in parallel trials in the presence of increasing amounts of IPTG (0, 5, 10, 15, 20, 30, 40, 50, 1000 µM). When an absorbance of 0.2 was reached, 0.2 µg/ml anhydracycline [tr. note #8] was added to induce transcription of the Intimin gene. The cells were harvested after one hour of induction. The cells were labeled successively with anti-Etag antibody, biotinylated goat anti-mouse antibody and, finally, with phycoerythrin-coupled streptavidin (see above). The fluorescence per cell which that causes is proportional to the number of Intimin-fusion proteins exposed on the surface of the cell. The cellular fluorescence was measured by flow cytometry. As FIG. 8 shows, the intensity of the fluorescence per cell, and thus the number of exposed molecules, is directly correlated with the amount of IPTG inducer. It can be modulated in other regions.

Example 2

Bacterial Surface Exposure of Protein Fragments, Epitope Mapping, and Isolation of Monospecific Antibodies The gene for PMS1 from the yeast S. cerevisiae (Gene Bank Accession Number M29688) was used as the model antigen. The gene (2.7 kB) was amplified using the PCR primers PMS1up (SEQ ID NO: 12) and PMS1lo (SEQ ID NO: 13) from S. cerevisiae. The DNA was purified with the Nucleotrap PCR kit (Machery and Nagel). The DNAse I digestion was carried out in four different trial solutions using $1.8 * 10^{-2}$, $2,7^?·$, $10^{-2}$, $3.6 * 10^{-2}$ and 0.18 υ DNAse I [tr. note #9] in the presence of 2 mM MnCl2.5 µg DNA was used per solution. The restriction cutting was stopped by addition of 500 mM EDTA after 10 minutes at room temperature. The resulting fragments were separated on a 12.5% polyacrylamide gel after staining with ethidium bromide. Fragments in the size range of 40–100 bp were cut out. Then the fragments were eluted from the gel by diffusion overnight in TBE buffer. Then any DNAse I that might still be present was removed by phenol/chloroform extraction and ethanol precipitation of the DNA. After that, overhanging ends were filled out with T4-DNA polymerase in the presence of dATP, dCTP, dGTP and dTTP. Then oligonucleotide hybrid linkers (see FIG. 10) were ligated to them (2.5 molar excess, 16 hours at 15° C.) and the ligation products were again purified on a 12.5% [poly]acrylamide gel.

Figures 10, 11, 13:
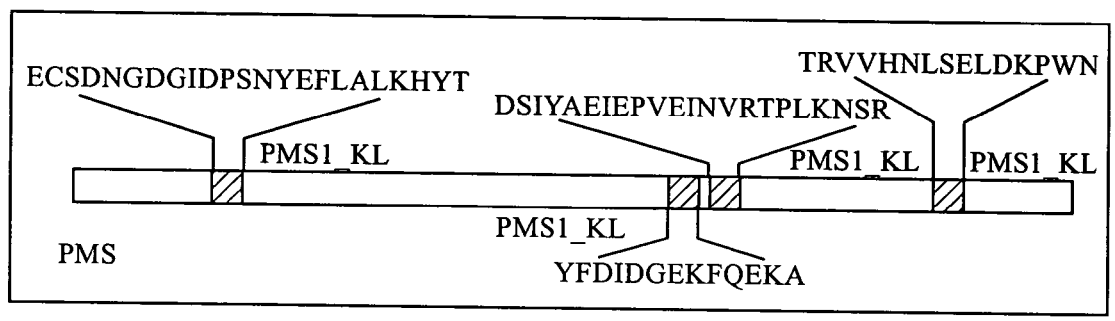
FIG. 10: Representation of the two linker molecules resulting from hybridization of 4 oligonucleotides, which generate the corresponding, vector cleavage sites (AvaI/BamHI). Coding strand of linker molecule on the left, SEQ ID NO:18. Coding strand of linker molecule on the right, SEQ ID NO:19.
FIG. 11: Position of the epitope identified in the protein sequence of PMS1. From left to right, epitope with sequence ECS . . . HYT, SEQ ID NO:20; epitope with sequence YFD . . . EKA, SEQ ID NO:21; epitope with sequence DSI . . . NSR, SEQ ID NO:22; epitope with sequence TRV . . . PWN, SEQ ID NO:23.
FIG. 13: Amino acid sequence of the library of EETI-II variants (SEQ ID NO:7). Amino acids in the single letter code. The two loop regions in which amino acid positions (X) are randomized are indicated in italics

The solution conditions were the same as in the purification of the gene fragments. Then the DNA was again extracted with phenol/chloroform and precipitated. The cloning vector pASK-INT-EETI-CKSend was cut with AvaI/BamHI and purified by centrifugation in a sucrose gradient (Kolmar, H. & Fritz, H.-J. (1995). Oligonucleotide-directed mutagenesis with single-stranded cloning vectors. In: DNA Cloning 1: A Practical Approach. D. Glover, B. D. Hames (Eds.), IRL Press, Oxford, pages 193–224). A total of 230 ng split vector was ligated with the fragmented DNA per gene bank, and electrocompetent BMH 71-18 cells were transformed with it. A collection of $7,2 * 10^4$ independent clones was obtained. The population of bacterial cells was incubated with polyclonal anti-PMS1 rabbit serum after induction of the expression of the Intimin fusion gene by addition of anhydrotetracycline. The specific binding of antibodies to epitope-carrying cells was determined by labeling with biotinylated anti-rabbit antibodies and incubation with streptavidin-phycoerythrin conjugate. Fluorescence-labeled cells were sorted by FACS and deposited individually on an agar plate with a MoFlo Cellsorter (Cytomation). DNA was prepared from a number of clones and the nucleotide sequences of four cloned PMS1 gene fragments were determined. The DNA sequence of the clones involves the bases 259–330 (PMS1_KL3), 1630–1672 (PMS1_KL6), 1786–1836 (PMS1_KL7) and 2590–2639 (PMS1_KL10) of the pms1 gene (a total of 2715 bp). FIG. 11 shows the positions of these epitopes in the peptide sequence of the PMS1 protein, as well as the translated amino acid sequence of the cloned PMS1 sequence segment.

Figure 12A:
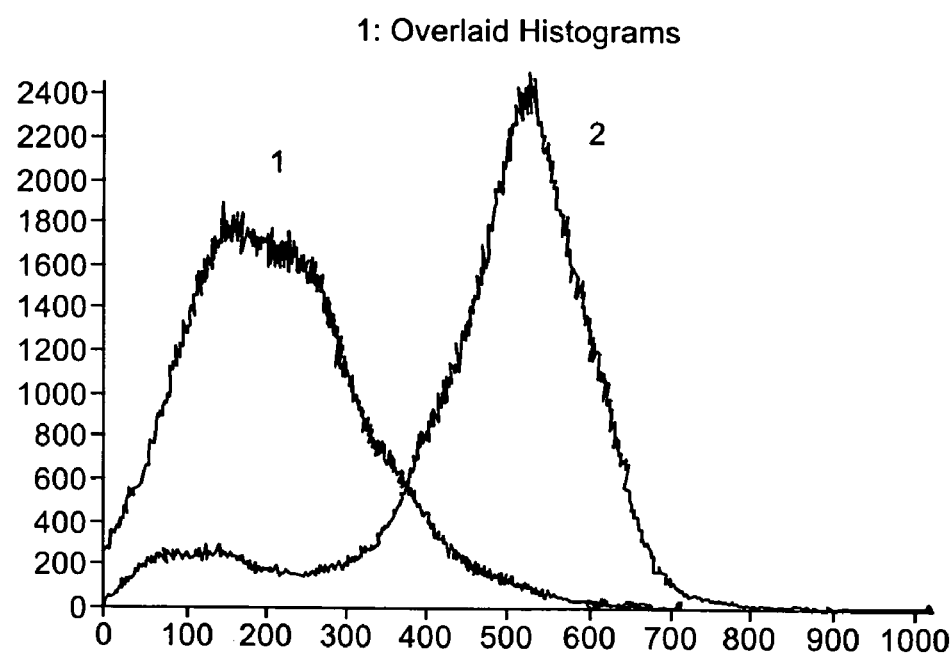
FIG. 12: A) PMS1_KL6 labeled with purified antibodies against clone 7 (1) and with purified antibodies against its own epitope (2); B) PMS1_KL7 labeled with purified antibodies against clone 6 and with purified antibodies against its own epitope (2).
Figure 12B:
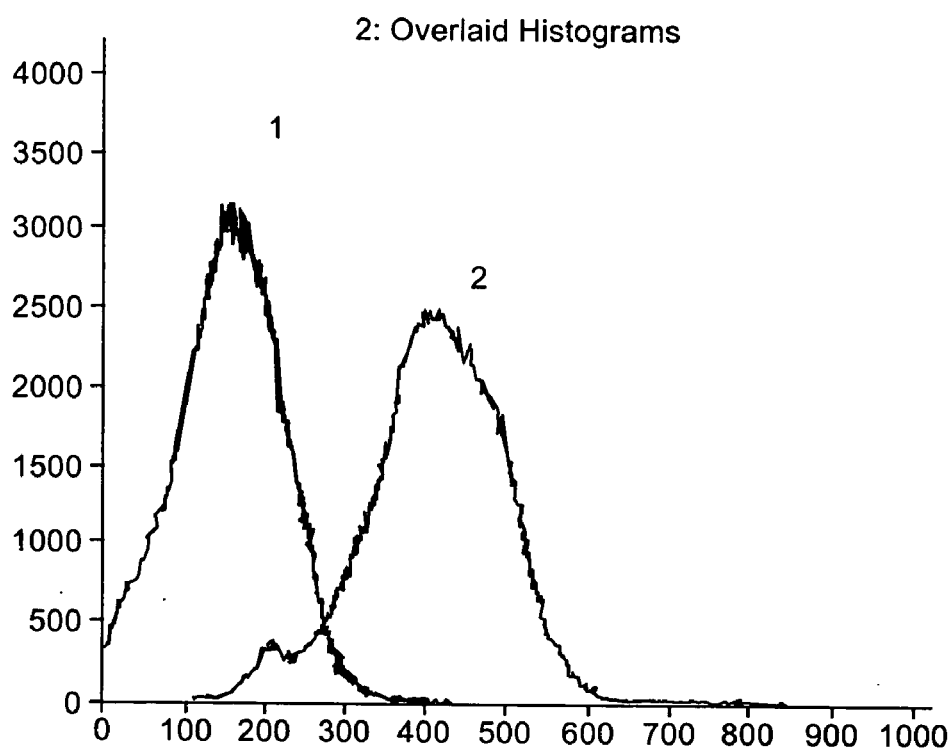

Cultures of the clones PMS_KL6 and PMS_KL7 were grown on the 50 ml scale. After one hour of induction by addition of anhydrotetracycline (02 µg/ml) at an absorbance of 0.2, the cells were pelleted, washed with PBS buffer, and resuspended in 500 µl PBS. Then 200 µl MS1 serum was added to these bacteria and the suspension was incubated on ice for 45 minutes. Then the cells were pelleted and the supernatant was discarded. The cell pellet was resuspended in 200 µl glycine/NaCl (0.2 M glycine, 0.145 M NaCl, pH 2.0), resuspended, and incubated for 45 minutes on ice. Following the incubation, the bacteria were centrifuged off. The supernatant was made alkaline by addition of 100 µl of 1 M Tris/HCl, pH 9. The cells of clone KL6 and KL7 were incubated with the monospecific antibodies obtained in this manner (see FIG. 12).

This shows that monospecific antibodies can be isolated with this procedure.

Example 3

Isolation of Peptides with Affinity to a Specified Target Protein by Intimin-based Surface Exposure of Combinatorial Peptide Libraries A library of variants of the cystine node protein EETI-II, comprising 28 amino acids, was generated. EETI-II is a trypsin protease inhibitor that occurs in the vegetable marrow Ecballium elaterium. This peptide is stabilized by three intramolecular disulfide bridges which produce a series of surface loops (described in Wentzel et al. (1999), J. Biol. Chem. 274: 21037–21043). A library of EETI-II variants was generated, in which the groups of two loop regions exposed to the solvent are randomized. The amino acid sequence of the EETI-II collection is: GCXXXXMRCK-QDSDCLAGCVCQVLXPXXSXCG (SEQ ID NO:7). (Amino acids in one-letter code. The two loop regions in which amino acid position(x)s are randomized are indicated in italics.)

The randomized eeti genes were generated using PCR. An eeti-ckSend gene (see above) was used as the template. It was amplified using the degenerate primer eti_4+4up (SEQ ID NO:14) and eti_4+4lo (SEQ ID NO:15). The randomization of the corresponding codons in the primer sequence occurred according to the pattern NNS, in which N represents one of the four nucleotides and S represents G or C. This selection excluded the stop codons ochre (TAA) and opal (TGA) and reduced the number of possible codons from 64 to 32, but they still code for all the amino acids. The mixture of resulting PCR products was cut with AvaI and BamHI and ligated with the vector fragment pASK-INT-EETI-CKSend cut with the AvaI/BamHI.

The pASK-INT-EETI-CKSend served as the cloning vector (see FIG. 8). This vector was cut with AvaI and BamHI. Then the vector fragment was separated from the vector DNA by means of sucrose gradient centrifugation. The eeti4+4 genes generated by PCR with degenerated primers were ligated with the purified vector and the E. coli strain DH5((Hanahn, d. (1983), J. Mol. Biol. 166: 557–580) was transformed with this solution. Sixteen transformations were done in parallel. All the transformants were streaked on selective plates containing chloramphenicol (25 µg/ml). After incubation for about 20 hours at 37° C., the colonies were suspended and the cells were stored as aliquots at −80° C. after addition of DMSO (7%). A total of $2*10^7$ independent clones was generated in this manner.

Figure 14A:
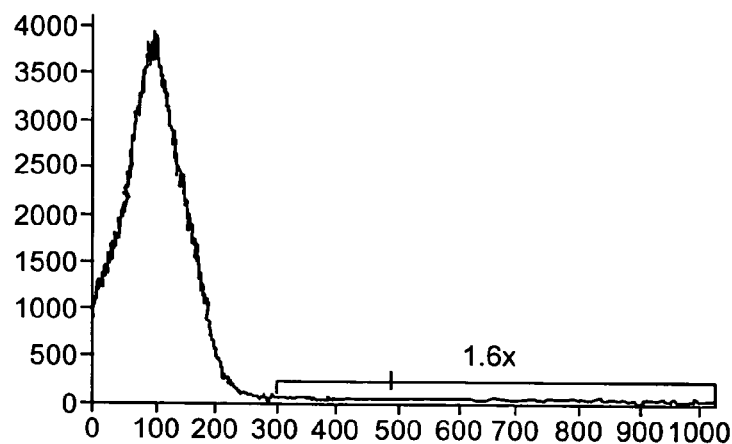
FIG. 14: Enrichment of the microproteins that bind the anti-β-lactamase antibodies. All of the cells were labeled with anti-β-lactamase as described in the text.
Figure 14B:
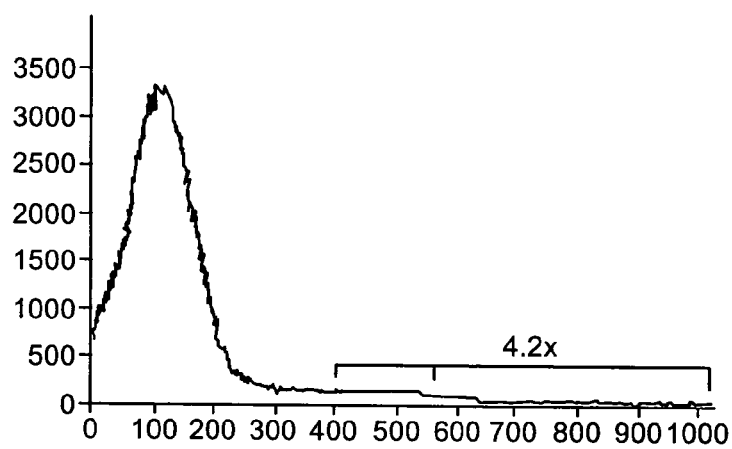
Figure 14C:
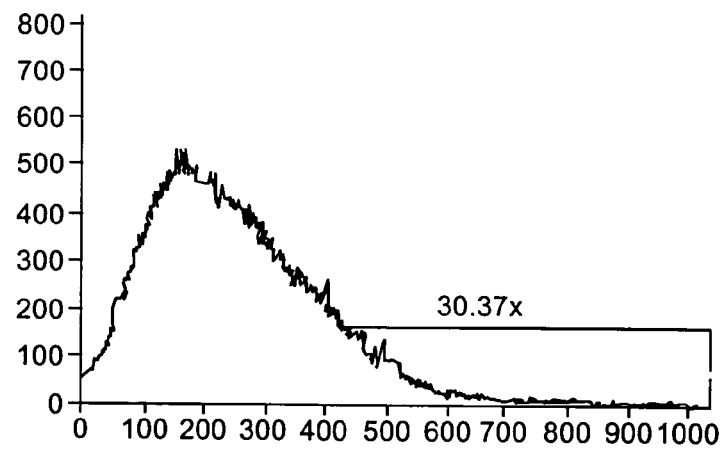

50 ml of liquid culture was inoculated with $10^9$ cells of the stored library to isolate microproteins with affinity to anti-β-lactamase antibodies. On reaching an absorbance of 0.4, anhydrotetracycline was added (0.2 µg/ml) to induce the gene expression. After induction, the cells were fluorescence-labeled. That was done by incubating the cells first for 10 minutes anti-β-lactamase antibodies and then washing them with PBS to remove unbound protein. Then the cells were incubated with biotinylated anti-rabbit antibodies and then with streptavidin-coupled R-phycoerythrin. After labeling the cells were analyzed in the Cellsorter, with fluorescent cells sorted out. Those bacteria which fell between 300 and 1024 in a fluorescence channel were defined as fluorescent (see FIG. 14).

Cells sorted out were plated on agar plates containing chloramphenicol (26 µg/ml) and incubated overnight at 37° C. The colonies were suspended on the following day and stored as DMSO culture at −80° C. One aliquot was used to inoculate a fresh 50 ml culture.

A total of $2*10^8$ cells was analyzed in the first round. Those which fell into the appropriate fluorescence channel (300–1024), were sorted out. In the second round, cells, which fell into this fluorescence channel (4.2% in all), were sorted out and then immediately resorted twice. These cells ($5*10^5$ events) were plated out and went to the third round on the next day. Here a significant increase of bacteria falling into the selected range was recorded (30%). The cells were again sorted and plated so that individual clones could be analyzed on the following day. Fifteen of twenty individual clones showed interaction with anti-β-lactamase. Plasmid DNA was isolated from 6 of these clones, and the nucleotide sequence of the gene for the EETI-CK variant was determined (FIG. 15).

Protein sequences from the Intimin family usable within the limits of this invention are described at the following locations in the literature:
1) Gamma Intimin (*Escherichia coli*), NCBI GI 3941710, NCBI GI 3941712, NCBI GI 3941714, McGraw, E. A., in "Molecular evolution and mosaic structure of alpha, beta Intimins of pathogenic *Escherichia coli*", Mol. Biol. Evol. 16 (1) 12–22 (1999).
2) Intimin (attaching and effacing protein, eae protein) NCBI GI 1169452, Yu, Ji and Kaper, J. B., in "Cloning and characterization of the eae gene of enterohae. *Escherichia coli* O157:H7", Mol. Microbiol. 6(3), 411–417 (1992).
3) eae gene, NCBI GI 384173, Beebakhee, G., et al. In "Cloning and nucleotide sequence of the eae gene homologue enterohemorrhagic *Escherichia coli* Serotype O157/H7", FEMS Microbiol. Lett. 91(1), 63–68 (1992).
4) Intimin (*Escherichia coli*), NCBI GI 2565325, Voss, E. et al. in "Translocated intimin receptors (Tir) of shiga-toxigenic *E. coli* isolates belonging to serogroups O26, O111 and O157 with sera from patients with hemolytic-uremic syndrome and marked sequence heterogeneity", Infect. Immun. 66(11), 5580–5586 (1998).
5) Intimin (*Escherichia coli*) NCBI GI 2865299, Elliott, S. J., et al. In "The complete sequence of the locus of enterocyte effacement from enteropathogenic *Escherichia coli* E2348/69", Mol. Microbiol. 28(1), 1–4 (1998).
6) Beta Intimin (*Escherichia coli*), NCBI GI 3941718, McGraw et al., loc. cit.
7) Intimin (*Escherichia coli*), NCBI GI 2739264, Deibel, D. et al. In "EspE, a novel secreted protein of attaching and effacing is directly translocated into infected host cells, whereas a trypsin-phosphorylated 90 kDa protein" [sic] Mol. Microbiol. 28(3), 463–474 (1998).
8) Intimin (*Escherichia coli*) NCBI GI 4388530
9) Intimin (*Escherichia coli*) NCBI GI 4388530
10) Intimin type epsilon (*Escherichia coli*) NCBI GI 6683770
11) Intimin NCBI GI 1947048
12) Intimin NCBI GI 4106360
13) Intimin (*Escherichia coli*) NCBI GI 6649538
14) Intimin (*Escherichia coli*) NCBI GI 2809548
15) Intimin (*Escherichia coli*) NCBI GI 7384863
16) Shares homology with the enteropathogenic *E. coli* (EPEC) attaching and effacing) gene, putative NCBI GI 304362
17) Intimin (*Escherichia coli*) NCBI GI 7384863.

Intiminup:
5'- GCGCTCTAGATAACGAGGGAAAAAAT-GATTACTCATGGTTGTTATAC -3' (SEQ ID NO:9)

Intilo 1:
5'- GCGCCAATTGCGCTGGCCTTGGTTTGATC -3' (SEQ ID NO: 8)

SupE2_Ecoup
5'- GCGCGAATTCACCAGAAAGCGTTGTACGG -3' (SEQ ID NO:10)

SupE2-Mlu-lo
5'-GCGCACGCGTAAGACGCGGCAGCGTCGC -3' (SEQ ID NO:11)

PMS1up
5'-GCGATGTTTCACCACATCG -3' (SEQ ID NO: 12)

PMS1lo:

5'-TCATATTTCGTAATCCTTC- 3' (SEQ ID NO:13)

eti-4+4up:
5'-GACGCCCGGGTGCNNSNNSNNSNNSATC-
CGTTGCAAACAGGACTCCG -3' (SEQ ID NO:14)

eti-4+4lo:
5'GCGCGCGGATCCGCASNNAGASNNSN-
NAGGSNNGAGAACCTGGCAAACGCAGCCA
GCCAG -3' (SEO ID NO:15)

---

SEQUENCE LISTING

<160> NUMBER OF SEQ ID NOS: 24

Figure 1:
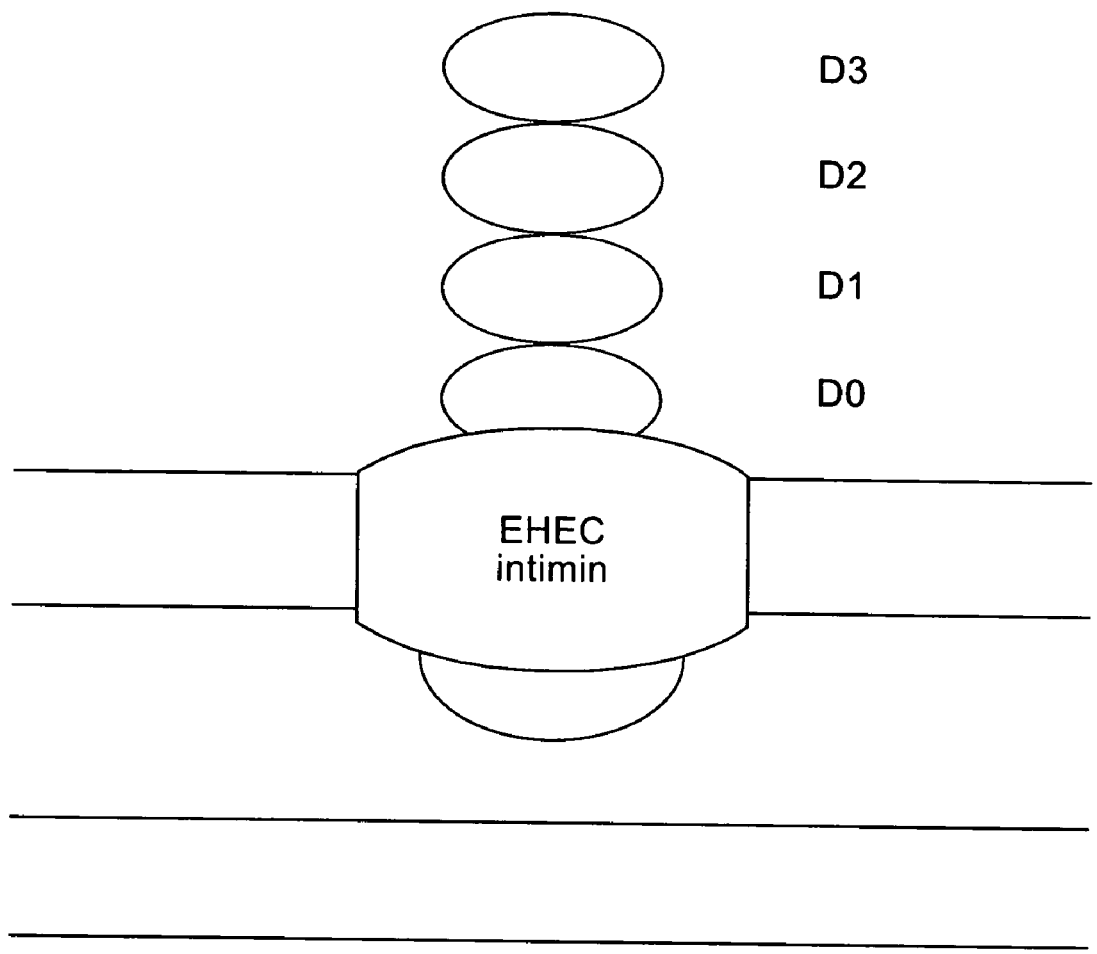
FIG. 1: Schematic representation of the structure of an Intimin. OM: external membrane; D0 to D3: extracellular domains 1 to 4. The Intimin fragment preferred here, which serves as the carrier for passenger domains, lacks domains D2 and D3.

<210> SEQ ID NO 1
<211> LENGTH: 32
<212> TYPE: PRT
<213> ORGANISM: Artificial
<220> FEATURE:
<223> OTHER INFORMATION: Ecballium elaterium, variant; figure 15-1

<400> SEQUENCE: 1

Gly Cys Val Met Thr Gly Ile Arg Cys Lys Gln Asp Ser Asp Cys Leu
1               5                   10                  15

Ala Gly Cys Val Cys Gln Val Leu Asn Pro Lys Thr Ser Asn Cys Gly
            20                  25                  30

Figure 5:
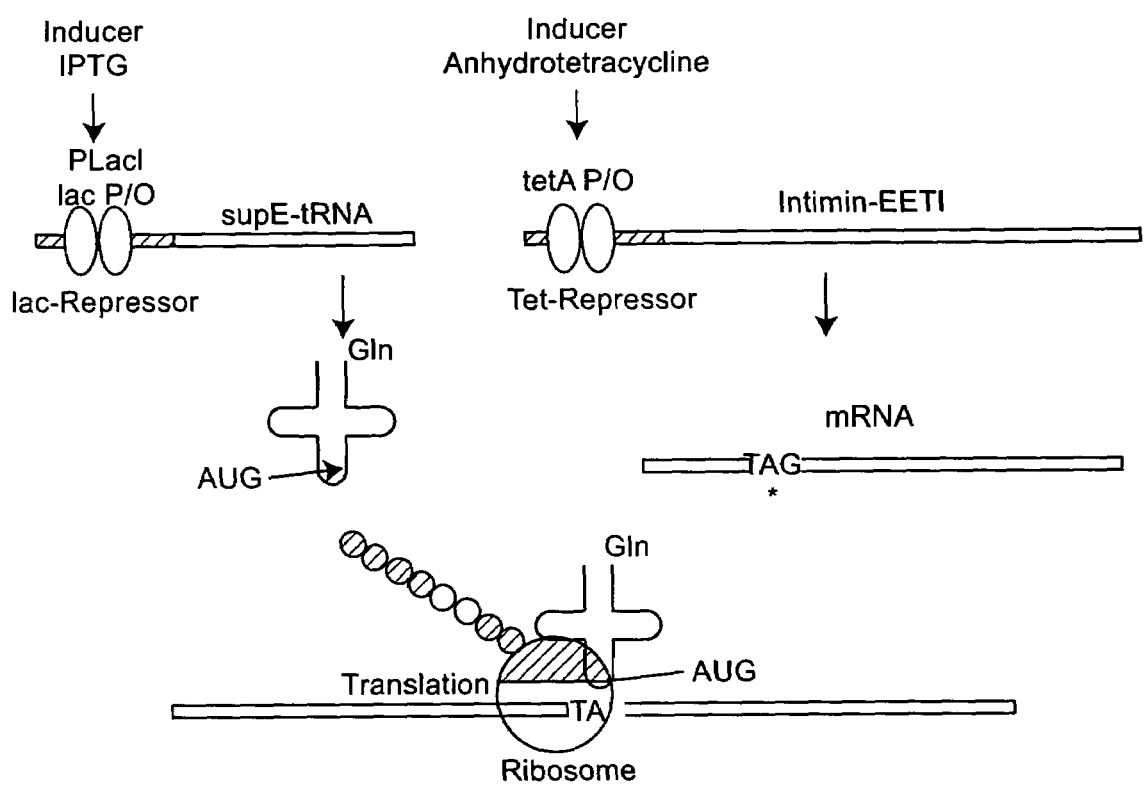
FIG. 5: Schematic representation of control of gene expression through supE-mediated translation control.

<210> SEQ ID NO 2
<211> LENGTH: 32
<212> TYPE: PRT
<213> ORGANISM: Artificial
<220> FEATURE:
<223> OTHER INFORMATION: Ecballium elaterium, variant; figure 15-5

<400> SEQUENCE: 2

Gly Cys Asn Arg Ser Leu Ile Arg Cys Lys Gln Asp Ser Asp Cys Leu
1               5                   10                  15

Ala Gly Cys Val Cys Gln Val Leu Asn Pro Pro Thr Ser Asn Cys Gly
            20                  25                  30

<210> SEQ ID NO 3
<211> LENGTH: 32
<212> TYPE: PRT
<213> ORGANISM: Artificial
<220> FEATURE:
<223> OTHER INFORMATION: Ecballium elaterium, variant; figure 15-8

<400> SEQUENCE: 3

Gly Cys Trp Glu Arg Asp Ile Arg Cys Lys Gln Asp Ser Asp Cys Leu
1               5                   10                  15

Ala Gly Cys Val Cys Gln Val Leu His Pro Ser Gln Ser Tyr Cys Gly
            20                  25                  30

Figure 9:
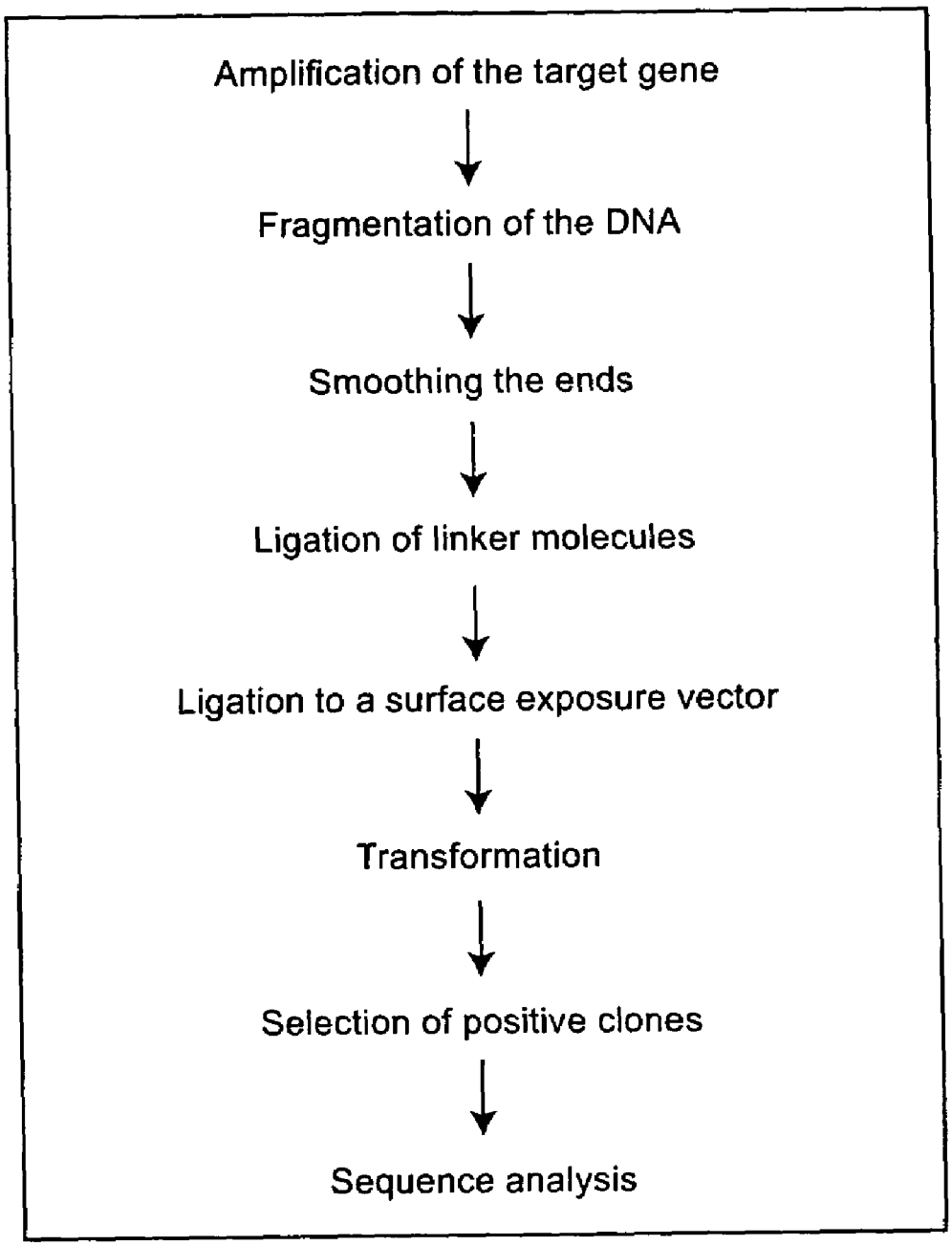
FIG. 9: Procedure for mapping of linear peptide epitopes.

<210> SEQ ID NO 4
<211> LENGTH: 32
<212> TYPE: PRT
<213> ORGANISM: Artificial
<220> FEATURE:
<223> OTHER INFORMATION: Ecballium elaterium, variant; figure 15-9

<400> SEQUENCE: 4

Gly Cys Val Thr Ser Leu Ile Arg Cys Lys Gln Asp Ser Asp Cys Leu
1               5                   10                  15

Ala Gly Cys Val Cys Gln Val Leu His Pro Pro Tyr Tyr Asn Cys Gly
            20                  25                  30

<210> SEQ ID NO 5
<211> LENGTH: 32
<212> TYPE: PRT

Figure 3:
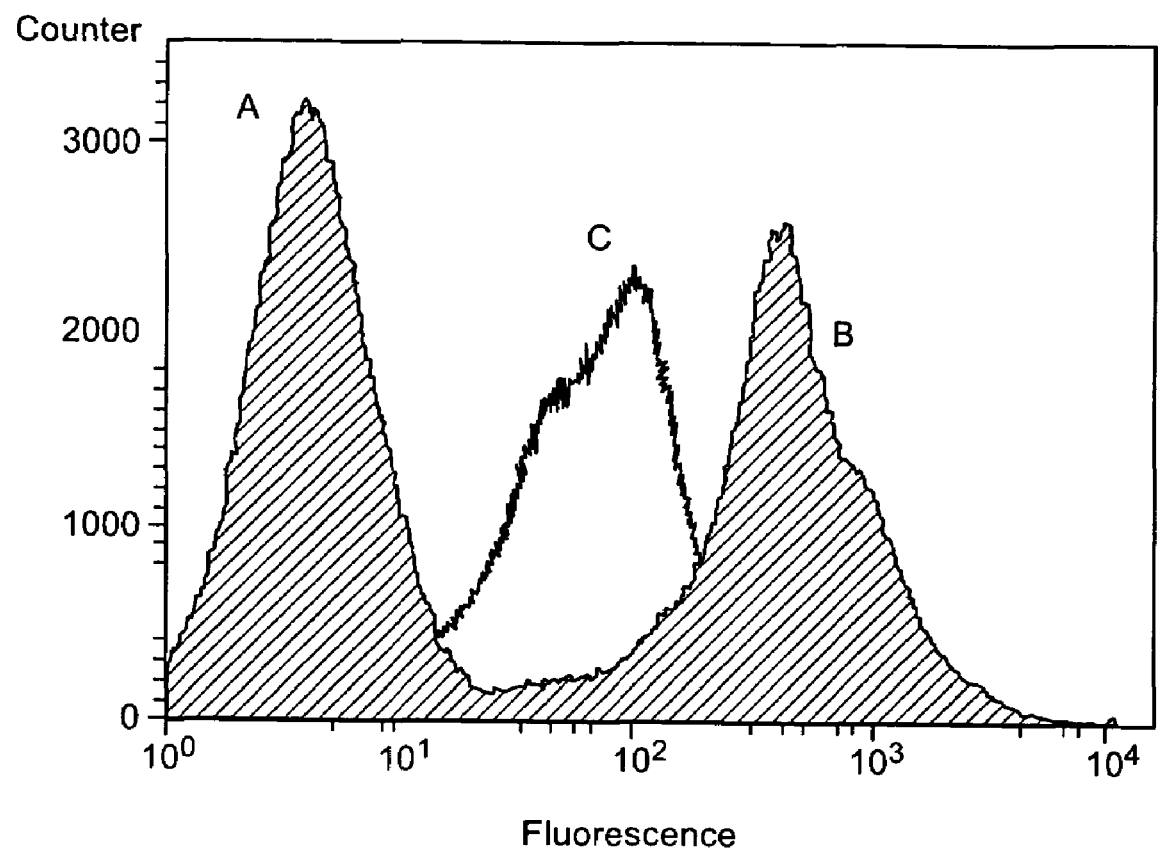
FIG. 3: Flow-cytometric analysis of the bacterial surface exposure of an Intimin-EETI-II microprotein fusion protein.
Figure 4:
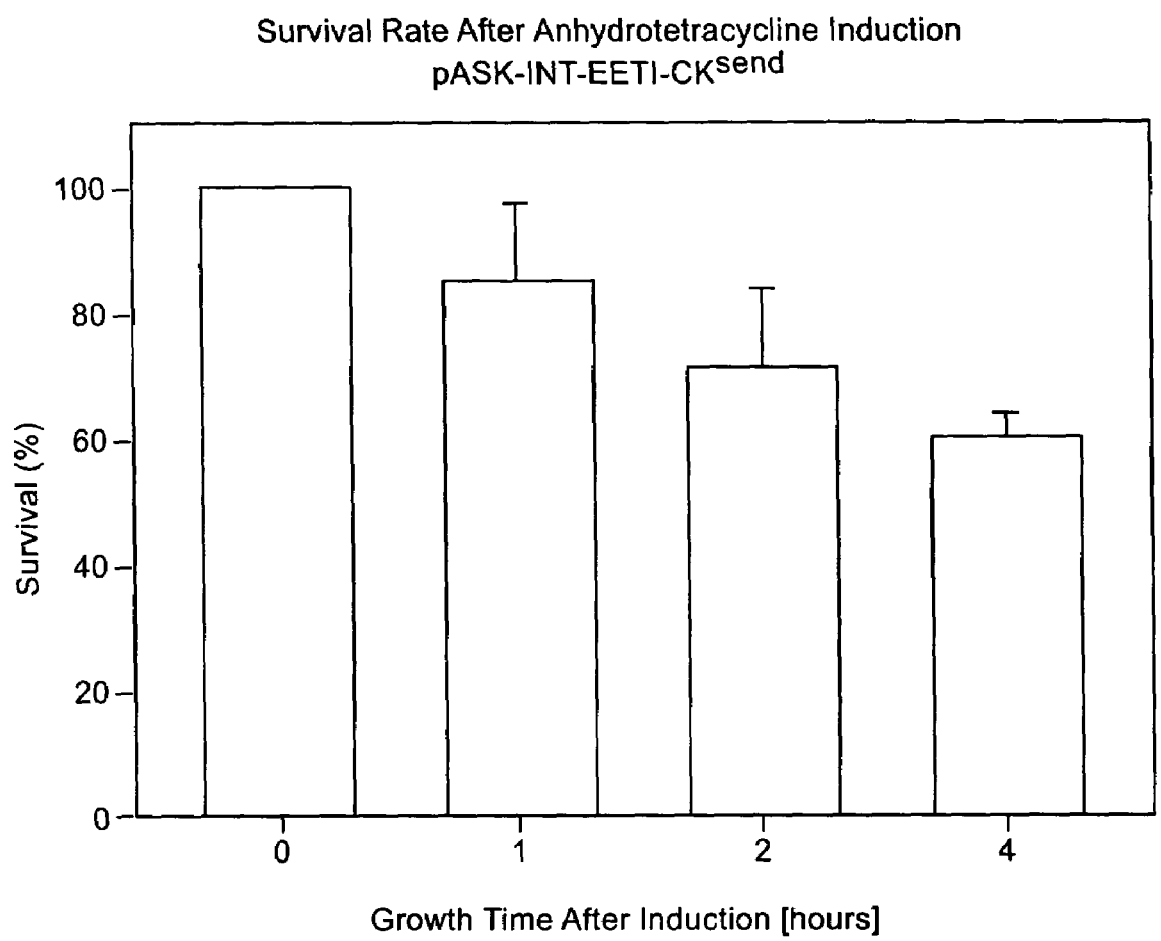
FIG. 4: Survival proportions of E. coli cells which expose a microprotein on the bacterial cell surface by means of the Intimin membrane anchor.

```
<213> ORGANISM: Artificial
<220> FEATURE:
<223> OTHER INFORMATION: Ecballium elaterium, variant; figure 15-3

<400> SEQUENCE: 5

Gly Cys Val Ser Ser His Ile Arg Cys Lys Gln Asp Ser Asp Cys Leu
1               5                   10                  15

Ala Gly Cys Val Cys Gln Val Leu His Pro Pro Tyr Gln Asn Cys Gly
            20                  25                  30

<210> SEQ ID NO 6
<211> LENGTH: 32
<212> TYPE: PRT
<213> ORGANISM: Artificial
<220> FEATURE:
<223> OTHER INFORMATION: Ecballium elaterium, variant; figure 15-7

<400> SEQUENCE: 6

Gly Cys Met Asp Thr His Ile Arg Cys Lys Gln Asp Ser Asp Cys Leu
1               5                   10                  15

Ala Gly Cys Val Cys Gln Val Leu Asn Pro Pro Thr Ser Asn Cys Gly
            20                  25                  30

<210> SEQ ID NO 7
<211> LENGTH: 32
<212> TYPE: PRT
<213> ORGANISM: Artificial
<220> FEATURE:
<223> OTHER INFORMATION: Ecballium elaterium, variant;
                        EETI-II Repertoire
<220> FEATURE:
<221> NAME/KEY: MISC_FEATURE
<222> LOCATION: (3)..(6)
<223> OTHER INFORMATION: X = A, R, N, D, C, Q, E, G, H, I, L, K, M, F,
                        P, S, T, W, Y, V
<220> FEATURE:
<221> NAME/KEY: MISC_FEATURE
<222> LOCATION: (25)..(25)
<223> OTHER INFORMATION: X = A, R, N, D, C, Q, E, G, H, I, L, K, M, F,
                        P, S, T, W, Y, V
<220> FEATURE:
<221> NAME/KEY: MISC_FEATURE
<222> LOCATION: (27)..(28)
<223> OTHER INFORMATION: X = A, R, N, D, C, Q, E, G, H, I, L, K, M, F,
                        P, S, T, W, Y, V
<220> FEATURE:
<221> NAME/KEY: MISC_FEATURE
<222> LOCATION: (30)..(30)
<223> OTHER INFORMATION: X = A, R, N, D, C, Q, E, G, H, I, L, K, M, F,
                        P, S, T, W, Y, V

<400> SEQUENCE: 7

Gly Cys Xaa Xaa Xaa Xaa Met Arg Cys Lys Gln Asp Ser Asp Cys Leu
1               5                   10                  15

Ala Gly Cys Val Cys Gln Val Leu Xaa Pro Xaa Xaa Ser Xaa Cys Gly
            20                  25                  30

<210> SEQ ID NO 8
<211> LENGTH: 29
<212> TYPE: DNA
<213> ORGANISM: Artificial
<220> FEATURE:
<223> OTHER INFORMATION: EHEC, variant; oligonucleotide Intilo 1

<400> SEQUENCE: 8
gcgccaattg cgctggcctt ggtttgatc                                    29

<210> SEQ ID NO 9
```

```
<211> LENGTH: 48
<212> TYPE: DNA
<213> ORGANISM: Artificial
<220> FEATURE:
<223> OTHER INFORMATION: EHEC, variant; oligonucleotide Intiminup

<400> SEQUENCE: 9
gcgctctaga taacgagggc aaaaaatgat tactcatggt tgttatac                48

<210> SEQ ID NO 10
<211> LENGTH: 29
<212> TYPE: DNA
<213> ORGANISM: Artificial
<220> FEATURE:
<223> OTHER INFORMATION: Escherichia coli, vairant; SupE2_coup

<400> SEQUENCE: 10
gcgcgaattc accagaaagc gttgtacgg                                     29

<210> SEQ ID NO 11
<211> LENGTH: 28
<212> TYPE: DNA
<213> ORGANISM: Artificial
<220> FEATURE:
<223> OTHER INFORMATION: Escherichia coli, variant; SupE2_Mlu-lo

<400> SEQUENCE: 11
gcgcacgcgt aagacgcggc agcgtcgc                                      28

<210> SEQ ID NO 12
<211> LENGTH: 19
<212> TYPE: DNA
<213> ORGANISM: Artificial
<220> FEATURE:
<223> OTHER INFORMATION: Saccharomyces cerevisiae, variant; PMS1up

<400> SEQUENCE: 12
gcgatgtttc accacatcg                                                19

<210> SEQ ID NO 13
<211> LENGTH: 19
<212> TYPE: DNA
<213> ORGANISM: Artificial
<220> FEATURE:
<223> OTHER INFORMATION: Saccharomyces cerevisiae, variant; PMS1lo

<400> SEQUENCE: 13
tcatatttcg taatccttc                                                19

<210> SEQ ID NO 14
<211> LENGTH: 47
<212> TYPE: DNA
<213> ORGANISM: Artificial
<220> FEATURE:
<223> OTHER INFORMATION: Oligodeoxyribonucleotide to the Amplification
                        and Mutation, artificial DNA-sequence from
                        Ecballium elaterium Trypsin Inhibitor II;
                        eti-4+4up
<220> FEATURE:
<221> NAME/KEY: misc_feature
<222> LOCATION: (14)..(15)
<223> OTHER INFORMATION: n = A, C, G, T
<220> FEATURE:
<221> NAME/KEY: misc_feature
<222> LOCATION: (16)..(16)
<223> OTHER INFORMATION: s = C, G
<220> FEATURE:
<221> NAME/KEY: misc_feature
<222> LOCATION: (17)..(18)
```

```
<223> OTHER INFORMATION: n = A, C, G, T
<220> FEATURE:
<221> NAME/KEY: misc_feature
<222> LOCATION: (19)..(19)
<223> OTHER INFORMATION: s = C, G
<220> FEATURE:
<221> NAME/KEY: misc_feature
<222> LOCATION: (20)..(21)
<223> OTHER INFORMATION: n = A, C, G, T
<220> FEATURE:
<221> NAME/KEY: misc_feature
<222> LOCATION: (22)..(22)
<223> OTHER INFORMATION: s = C, G
<220> FEATURE:
<221> NAME/KEY: misc_feature
<222> LOCATION: (23)..(24)
<223> OTHER INFORMATION: n = A, C, G, T
<220> FEATURE:
<221> NAME/KEY: misc_feature
<222> LOCATION: (25)..(25)
<223> OTHER INFORMATION: s = C, G

<400> SEQUENCE: 14
gacgcccggg tgcnnsnnsn nsnnsatccg ttgcaaacag gactccg          47

<210> SEQ ID NO 15
<211> LENGTH: 60
<212> TYPE: DNA
<213> ORGANISM: Artificial
<220> FEATURE:
<223> OTHER INFORMATION: Oligodeoxyribonucleotide to the Amplification
                        and Mutation, artificial DNA Sequence from
                        Ecballium elaterium Trypsin Inhibitor II;
                        eti-4+4lo
<220> FEATURE:
<221> NAME/KEY: misc_feature
<222> LOCATION: (16)..(16)
<223> OTHER INFORMATION: s = C, G
<220> FEATURE:
<221> NAME/KEY: misc_feature
<222> LOCATION: (17)..(18)
<223> OTHER INFORMATION: n = A, C, G, T
<220> FEATURE:
<221> NAME/KEY: misc_feature
<222> LOCATION: (22)..(22)
<223> OTHER INFORMATION: s = C, G
<220> FEATURE:
<221> NAME/KEY: misc_feature
<222> LOCATION: (23)..(24)
<223> OTHER INFORMATION: n = A, C, G, T
<220> FEATURE:
<221> NAME/KEY: misc_feature
<222> LOCATION: (25)..(25)
<223> OTHER INFORMATION: s = C, G
<220> FEATURE:
<221> NAME/KEY: misc_feature
<222> LOCATION: (26)..(27)
<223> OTHER INFORMATION: n = A, C, G, T
<220> FEATURE:
<221> NAME/KEY: misc_feature
<222> LOCATION: (31)..(31)
<223> OTHER INFORMATION: s = C, G
<220> FEATURE:
<221> NAME/KEY: misc_feature
<222> LOCATION: (32)..(33)
<223> OTHER INFORMATION: n = A, C, G, T

<400> SEQUENCE: 15
gcgcgcggat ccgcasnnag asnnsnnagg snngagaacc tggcaaacgc agccagccag   60

<210> SEQ ID NO 16
<211> LENGTH: 644
<212> TYPE: DNA
<213> ORGANISM: Escherichia coli
<220> FEATURE:
```

```
<221> NAME/KEY: SupE-Eco
<222> LOCATION: (1)..(644)

<400> SEQUENCE: 16
caccagaaag cgttgtacgg atggggtatc gccaagcggt aaggcaccgg tttttgatac      60
cggcattccc tggttcgaat ccaggtaccc cagccatctt cttcgagtaa gcggttcacc     120
gcccggttat tggggtatcg ccaagcgtta aggcaccggt ttttgatacc ggcattccct     180
ggttcgaatc caggtacccc agccatcgaa gaaacaatct ggctacgtag ctcagttggt     240
tagagcacat cactcataat gatggggtca caggttcgaa tcccgtcgta gccaccaaat     300
tctgaatgta tcgaatatgt tcggcaaatt caaaaccaat ttgttggggt atcgccaagc     360
ggtaaggcac cggattctaa ttccggcatt ccgaggttcg aatcctcgta ccccagccaa     420
tttattcaag acgcttacct tgtaagtgca cccagttggg gtatcgccaa gcggtaaggc     480
accggattct gattccggca ttccgaggtt cgaatcctcg taccccagcc acattaaaaa     540
agctcgcttc ggcgagcttt tgcttttct gcgttcattc aatgtcgaat gcgatgttga      600
cacgtcttat ccttcaatgt cggatgcgac gctgccgcgt ctta                      644

<210> SEQ ID NO 17
<211> LENGTH: 2238
<212> TYPE: DNA
<213> ORGANISM: Artificial
<220> FEATURE:
<223> OTHER INFORMATION: Hybrid of tetA promotor region ASK75), Intimin
                        EaeA fragment of EHEC, E-tag epitope, variant
                        from EETI-II (Ecballium elaterium
                        trypsin Inhibitor) with internal Epitpoe of
                        Sendai Virus
<220> FEATURE:
<221> NAME/KEY: Promotor/Operator (tetA)
<222> LOCATION: (1)..(78)
<220> FEATURE:
<221> NAME/KEY: Intimin-fragment
<222> LOCATION: (79)..(2076)
<220> FEATURE:
<221> NAME/KEY: E-tag
<222> LOCATION: (2077)..(2130)
<220> FEATURE:
<221> NAME/KEY: ETI-send
<222> LOCATION: (2131)..(2238)

<400> SEQUENCE: 17
tattttacca ctccctatca gtgatagaga aaagtgaaat gaatagttcg acaaaaatct      60
agataacgag ggcaaaaaat gattactcat ggttgttata cccggacccg gcacaagcat     120
aagctaaaaa aaacattgat tatgcttagt gctggtttag gattgttttt ttatgttaat     180
tagaattcat ttgcaaatgg tgaaaattat tttaaattgg gttcggattc aaaactgtta     240
actcatgata gctatcagaa tcgcctttttt tatacgttga aaactggtga aactgttgcc     300
gatctttcta aatcgcaaga tattaattta tcgacgattt ggtcgttgaa taagcatttta    360 tacagttctg aaagcgaaat gatgaaggcc gcgcctggtc agcagatcat tttgccactc     420
aaaaaacttc ccttttgaata cagtgcacta ccactttttag gttcggcacc tcttgttgct    480
gcaggtggtg ttgctggtca cacgaataaa ctgactaaaa tgtccccgga cgtgaccaaa     540
agcaacatga ccgatgacaa ggcattaaat tatgcggcac aacaggcggc gagtctcggt    600
agccagcttc agtcgcgatc tctgaacggc gattacgcga agataccgc tcttggtatc      660 gctggtaacc aggcttcgtc acagttcag gcctggttac aacattatgg aacggcagag     720
gttaatctgc agagtggtga taactttgac ggtagttcac tggacttctt attaccgttc     780
```

```
tatgattccg aaaaaatgct ggcatttggt caggtcggag cgcgttacat tgactcccgc    840
tttacggcaa atttaggtgc gggtcagcgt tttttccttc ctgcaaacat gttgggctat    900
aacgtcttca ttgatcagga ttttctggt gataataccc gtttaggtat tggtggcgaa    960
tactggcgag actatttcaa agtagcgtt aacggctatt ccgcatgag gcgctggcat    1020 gagtcatacc ataagaaaga ctatgatgag cgcccagcaa atggcttcga tatccgtttt    1080
aatggctatc taccgtcata tccggcatta ggcgccaagc tgatatatga gcagtattat    1140
ggtgataatg ttgctttgtt taattctgat aagctgcagt cgaatcctgg tgcggcgacc    1200
gttggtgtaa actatactcc gattcctctg gtgacgatgg ggatcgatta ccgtcatggt    1260
acgggtaatg aaaatgatct cctttactca atgcagttcc gttatcagtt tgataaatcg    1320
tggtctcagc aaattgaacc acagtatgtt aacgagttaa gaacattatc aggcagccgt    1380
tacgatctgg ttcagcgtaa taacaatatt attctggagt acaagaagca ggatattctt    1440
tctctgaata ttccgcatga tattaatggt actgaacaca gtacgcagaa gattcagttg    1500
atcgttaaga gcaaatacgg tctggatcgt atcgtctggg atgatagtgc attacgcagt    1560
cagggcggtc agattcagca tagcggaagc caaagcgcac aagactacca ggctattttg    1620
cctgcttatg tgcaaggtgg cagcaatatt tataaagtga cggctcgcgc ctatgaccgt    1680
aatggcaata gctctaacaa tgtacagctt actattaccg ttctgtcgaa tggtcaagtt    1740
gtcgaccagg ttggggtaac ggactttacg gcggataaga cttcggctaa agcggataac    1800
gccgatacca ttacttatac cgcgacggtg aaaaagaatg gggtagctca ggctaatgtc    1860
cctgtttcat ttaatattgt ttcaggaact gcaactcttg gggcaaatag tgccaaaacg    1920
gatgctaacg gtaaggcaac cgtaacgttg aagtcgagta cgccaggaca ggtcgtcgtg    1980
tctgctaaaa ccgcggagat gagttcagca cttaatgcca gtgcggttat attttttgat    2040
caaaccaagg ccagcgcaat tcctccaacg cccctgggtg cgccggtacc gtatccagat    2100
ccgctggaac cgcgtgccgc ttctggcccc gggtgcgatg gaagcttagg tgatatcgaa    2160
ccatacgatt catcatgcaa acaggactcc gactgcctgg ctggctgcgt ttgcgggccc    2220
aacggtttct gcggatcc                                                  2238
```

<210> SEQ ID NO 18
<211> LENGTH: 23
<212> TYPE: DNA
<213> ORGANISM: Artificial
<220> FEATURE:
<223> OTHER INFORMATION: Coding strand of linker molecule in figure 10A

<400> SEQUENCE: 18
ccgggtccgg aagcggttcc ggg                                             23

<210> SEQ ID NO 19
<211> LENGTH: 18
<212> TYPE: DNA
<213> ORGANISM: Artificial
<220> FEATURE:
<223> OTHER INFORMATION: Coding strand of linker molecule in Figure 10B.

<400> SEQUENCE: 19
taactgactg acccgcag                                                   18

<210> SEQ ID NO 20
<211> LENGTH: 23
<212> TYPE: PRT

```
<213> ORGANISM: Saccharomyces cerevisiae
<220> FEATURE:
<221> NAME/KEY: MISC_FEATURE
<222> LOCATION: (1)..(23)
<223> OTHER INFORMATION: epitope in protein sequence of PMS1, Figure 11

<400> SEQUENCE: 20

Glu Cys Ser Asp Asn Gly Asp Gly Ile Asp Pro Ser Asn Tyr Glu Phe
1               5                   10                  15

Leu Ala Leu Lys His Tyr Thr
            20

<210> SEQ ID NO 21
<211> LENGTH: 13
<212> TYPE: PRT
<213> ORGANISM: Saccharomyces cerevisiae
<220> FEATURE:
<221> NAME/KEY: MISC_FEATURE
<222> LOCATION: (1)..(13)
<223> OTHER INFORMATION: epitope in the protein sequence of PMS1,
                        Figure 11

<400> SEQUENCE: 21

Tyr Phe Asp Ile Asp Gly Glu Lys Phe Gln Glu Lys Ala
1               5                   10

<210> SEQ ID NO 22
<211> LENGTH: 22
<212> TYPE: PRT
<213> ORGANISM: Saccharomyces cerevisiae
<220> FEATURE:
<221> NAME/KEY: MISC_FEATURE
<222> LOCATION: (1)..(22)
<223> OTHER INFORMATION: epitope in the protein sequence of PMS1;
                        Figure 11

<400> SEQUENCE: 22

Asp Ser Ile Tyr Ala Glu Ile Glu Pro Val Glu Ile Asn Val Arg Thr
1               5                   10                  15

Pro Leu Lys Asn Ser Arg
            20

<210> SEQ ID NO 23
<211> LENGTH: 15
<212> TYPE: PRT
<213> ORGANISM: Saccharomyces cerevisiae
<220> FEATURE:
<221> NAME/KEY: MISC_FEATURE
<222> LOCATION: (1)..(15)
<223> OTHER INFORMATION: epitope in the protein seuqnece PMS1; Figure 11

<400> SEQUENCE: 23

Thr Arg Val Val His Asn Leu Ser Glu Leu Asp Lys Pro Trp Asn
1               5                   10                  15

Figure 2B:
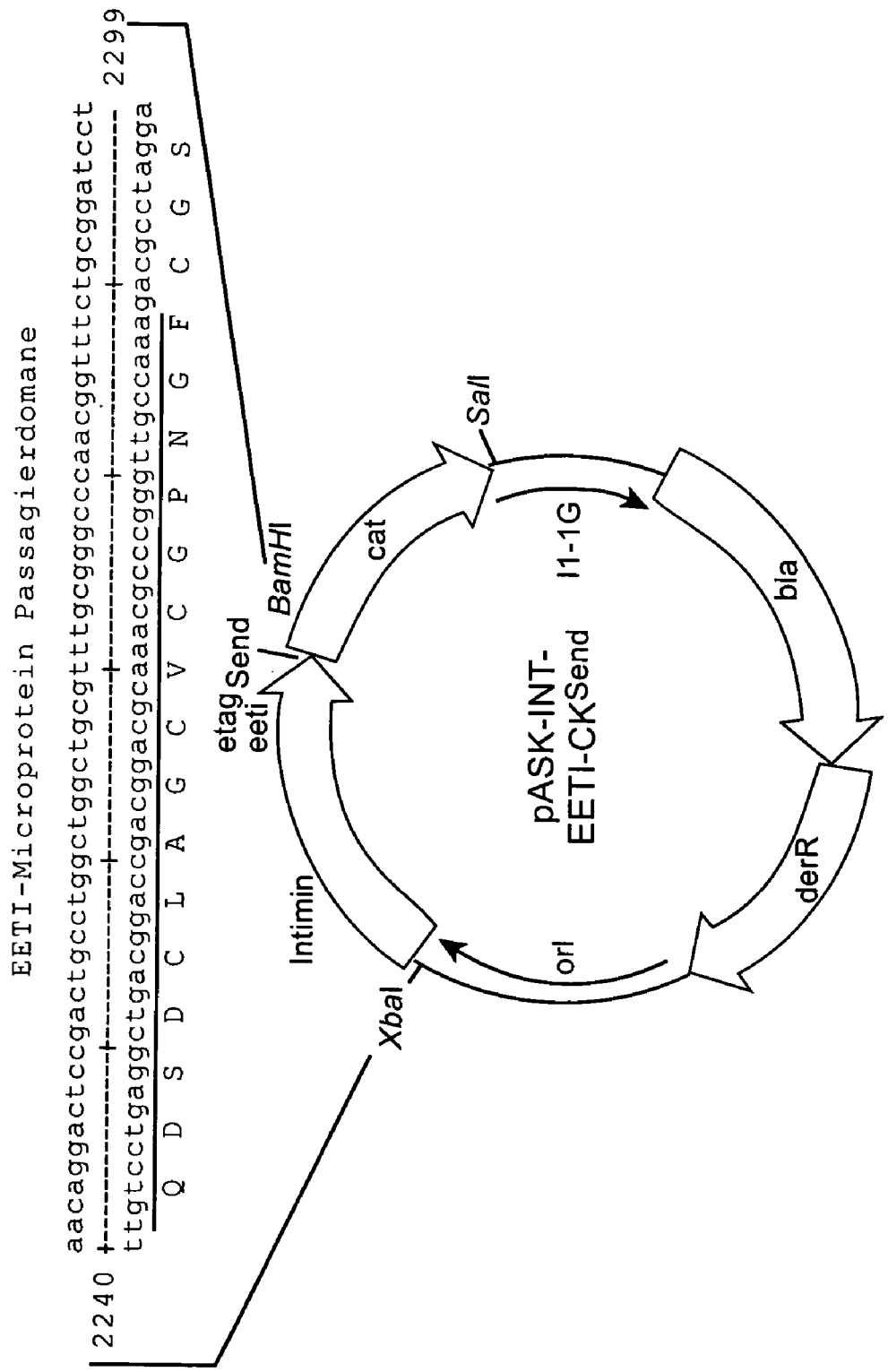
FIG. 2: Schematic representation of the expression vector pASK-INT-EETI-CKSend. Intimin: coding sequence for the Intimin gene fragment (SEQ ID NO: 17); etag: coding sequence for an epitope sequence (Etag); ead: coding sequence for the EETI-II microprotein; cat: gene for chloramphenicol acetyltransferase; tetR: gene for Tet repressor; bla: gene for β-lactamase. Corresponding translated amino acid sequence is SEQ ID NO:24.

<210> SEQ ID NO 24
<211> LENGTH: 108
<212> TYPE: PRT
<213> ORGANISM: Escherichia coli
<220> FEATURE:
<221> NAME/KEY: MISC_FEATURE
<222> LOCATION: (1)..(108)
<223> OTHER INFORMATION: corresponding translated amino acid sequence;
                        Figure 2

<400> SEQUENCE: 24

Met Ile Thr His Gly Cys Tyr Thr Arg Thr Arg His Lys His Lys Leu
1               5                   10                  15
```

-continued

```
Lys Lys Thr Leu Ile Met Leu Ser Ala Gly Leu Gly Leu Phe Phe Tyr
            20              25              30

Val Asn Asn Ser Phe Ala Asn Gly Phe Asp Gln Thr Lys Ala Ser Ala
            35              40              45

Ile Pro Pro Thr Pro Leu Gly Ala Pro Val Pro Tyr Pro Asp Pro Leu
    50              55              60

Glu Pro Arg Ala Ala Ser Gly Pro Gly Cys Asp Gly Ser Leu Gly Asp
65              70              75              80

Leu Glu Pro Tyr Asp Ser Ser Cys Lys Gln Asp Ser Asp Cys Leu Ala
            85              90              95

Gly Cys Val Cys Gly Pro Asn Gly Phe Cys Gly Ser
            100             105
```

The invention claimed is:

1. A process for exposing peptides and proteins on the surface of host bacteria, comprising the steps of
   (a) preparing a Gram-negative host bacterium that is transformed with a vector on which a fused nucleic acid sequence is localized which is in operative linkage with an exogenously inducible promoter, wherein said fused nucleic acid sequence codes for
      (i) a membrane anchoring domain which is an Intimin shortened by at least the D3 domain in the carboxy-terminal region, and
      (ii) a heterologous passenger peptide or passenger polypeptide to be exposed on the surface of the host bacterium, and
   (b) cultivating the host bacterium under conditions in which the heterologous passenger peptide or passenger polypeptide is expressed and exposed on the surface of the host bacterium.

2. A process according to claim 1, wherein the shortened Intimin membrane anchoring domain is shortened by at least one other Intimin domain selected from the group consisting of D0, D1, and D2.

3. A process according to claim 1, wherein the shortened Intimin membrane anchoring domain is from Enterobacteriaceae and the host bacterium is an Enterobacteriaceae.

4. A process according to claim 3, wherein the shortened Intimin membrane anchoring domain is from enterohemorrhagic *Escherichia coli*.

5. A process according to claim 4, wherein said enterohemorrhagic *Escherichia coli* is *Escherichia coli* O157:H7.

6. A process according to claim 5, wherein the shortened Intimin membrane anchoring domain contains amino acids 1 to 659 (SEQ ID NO: 25) of *Escherichia coli* O157:H7 Intimin.

7. A process according to claim 5, wherein the shortened Intimin membrane anchoring domain contains amino acids 1 to 753 (SEQ ID NO: 26) of *Escherichia coli* O157:H7 Intimin.

8. A process according to claim 1, in which expression of the fused nucleic acid sequence can be controlled, whereby
   (i) a codon of a nucleic acid sequence coding for the shortened Intimin membrane anchoring domain which codes for glutamine is replaced by an amber stop codon (TAG), and
   (ii) an *Escherichia coli* host strain is used in which translation of the mRNA of the fused nucleic acid sequence is accomplished by providing a controllable amount of suppressor tRNA which allows over-reading of the stop codon in the translation.

9. A process according to claim 8, in which regulation of the expression of a gene for the amber suppressor tRNA takes place due to the fact that it is placed under control of a promoter which is controllable in its transcription rate.

10. A process according to claim 9, in which the promoter, which is controllable in its transcription rate, is the PLlac promoter.

11. A process for producing a variant population of surface-exposed peptides/polypeptides/proteins with a desired property in host bacteria, and identifying host bacteria which expose the passenger peptide/polypeptide/protein stably on their surfaces, comprising the steps of:
   (i) producing one or more fusion genes or fusion gene fragments by cloning a coding sequence of a passenger peptide/polypeptide/protein in a continuous reading frame with a coding sequence of a shortened Intimin gene in at least one expression vector, wherein said shortened Intimin is shortened by at least the D3 carboxyterminal domain;
   (ii) varying the passenger peptide/polypeptide/protein by one of the methods selected from: intentional site-directed mutagenesis through the polymerase chain reaction (PCR) using oligonucleotides with intentionally exchanged bases, by random mutagenesis using oligonucleotides with randomly generated base sequences in selected sequence segments in the PCR, through error-prone PCR, randomly controlled chemical and radiation-generated mutagenesis,
   (iii) introducing the at least one expression vector into the host bacteria which expose the passenger peptide/polypeptide/protein stably on their surfaces,
   (iv) expressing the one or more fusion genes or fusion gene fragments in the host bacteria,
   (v) cultivating the bacteria to produce a stable surface-exposed passenger peptide/polypeptide/protein and,
   (vi) identifying host bacteria which carry a passenger peptide/polypeptide/protein with a desired property on their surface.

12. A process according to claim 11, which further comprises: (vii) selective enrichment of the host bacteria which carry the passenger peptide/polypeptide/protein with the desired property on their surface.

13. A process according to claim 11 in which the identification of bacteria which carry a passenger peptide/polypeptide/protein with a desired binding affinity exposed on the surface is accomplished by binding to a binding partner that is immobilized or labeled, or both.

14. A process according to claim 11, in which a population of bacteria which carry a surface-exposed passenger peptide/polypeptide/protein with a binding affinity to a binding partner is used as a matrix for affinity chromatography purification of binding partners from a mixture of substances.

15. An expression vector for the expression of a fusion gene under the control of an exogeneously inducible promoter in which there is, in operative linkage with the promoter, a coding sequence for a desired passenger peptide in a continuous reading frame downstream to a coding sequence for an Intimin membrane anchoring domain, wherein said Intimin membrane anchoring domain is shortened by at least the D3 domain in the carboxy-terminal region of 280 amino acids.

16. An expression vector according to claim 15, in which the promoter is selected from the group consisting of lac promoter, ara promoter, and tetA promoter.

17. A gram-negative host bacterium of the family Enterobactericeae, transformed with at least one expression vector according to claim 15.

18. A process according to claim 12, in which the identification of bacteria which carry a passenger peptide/polypeptide/protein with a desired binding affinity exposed on the surface is accomplished by binding to a binding partner that is immobilized or labeled, or both.

19. A process according to claim 12, in which a population of bacteria which carry a surface-exposed passenger peptide/polypeptide/protein with a binding affinity to a binding partner is used as a matrix for affinity chromatography purification of binding partners from a mixture of substances.

* * * * *